(12) United States Patent
Mohanlal et al.

(10) Patent No.: US 11,857,522 B2
(45) Date of Patent: Jan. 2, 2024

(54) COMPOSITIONS CONTAINING TUCARESOL OR ITS ANALOGS

(71) Applicant: BeyondSpring Pharmaceuticals, Inc., New York, NY (US)

(72) Inventors: Ramon Mohanlal, New York, NY (US); Lan Huang, New York, NY (US); George Kenneth Lloyd, New York, NY (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 218 days.

(21) Appl. No.: 17/170,058

(22) Filed: Feb. 8, 2021

(65) Prior Publication Data

US 2021/0161844 A1 Jun. 3, 2021

Related U.S. Application Data

(62) Division of application No. 16/075,942, filed as application No. PCT/US2017/016740 on Feb. 6, 2017, now Pat. No. 10,912,748.

(60) Provisional application No. 62/292,763, filed on Feb. 8, 2016.

(51) Int. Cl.
*A61K 31/192* (2006.01)
*A61P 35/00* (2006.01)
*A61K 31/496* (2006.01)
*A61K 39/395* (2006.01)
*C07K 16/28* (2006.01)
*A61K 39/00* (2006.01)

(52) U.S. Cl.
CPC .......... *A61K 31/192* (2013.01); *A61K 31/496* (2013.01); *A61K 39/3955* (2013.01); *A61P 35/00* (2018.01); *C07K 16/2818* (2013.01); *C07K 16/2827* (2013.01); *A61K 2039/505* (2013.01)

(58) Field of Classification Search
CPC .................................................. A61K 31/192
See application file for complete search history.

(56) References Cited

U.S. PATENT DOCUMENTS

| | | | |
|---|---|---|---|
| 4,410,537 A * | 10/1983 | Kneen | C07C 65/30 562/463 |
| 4,535,183 A | 8/1985 | Kneen | |
| 5,607,934 A | 3/1997 | Tone et al. | |
| 5,733,888 A | 12/1998 | Bryans et al. | |
| 5,852,018 A | 12/1998 | Bryans et al. | |
| 5,872,151 A | 2/1999 | Rhodes | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 5,958,980 A | 9/1999 | Rhodes | |
| 6,069,146 A | 5/2000 | Fenical et al. | |
| 6,096,786 A * | 8/2000 | Rhodes | A61K 31/192 514/568 |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 | 6/2006 | Hayashi et al. | |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |
| 7,700,615 B2 | 4/2010 | Edwards et al. | |
| 7,919,497 B2 | 4/2011 | Palladino et al. | |
| 7,935,704 B2 | 5/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |

(Continued)

FOREIGN PATENT DOCUMENTS

| CN | 110240592 | 9/2017 |
|---|---|---|
| EA | 010198 B1 | 6/2008 |

(Continued)

OTHER PUBLICATIONS

Nicholson et al. Anticancer Drugs, 2006, 17(1): 25-31 (abstract).*
"Definition of 'within'". [Online] [2015 Archived version accessed on Aug. 13, 2020 from https://web.archive.org/web/20151030162428/https://dictionary.cambridge.org/us/dictionary/english/within. Cambridge English Dictionary. (Year: 2015).
Abels, Christoph, Targeting of the Vascular System of Solid Tumours by Photodynamic Therapy (PDT), Photochem Photobiol Sci., (Mar. 2004) 3: 765-771.
Abolhasani et al., Jan. 2015, In-silico investigation of tubulin binding modes of a series of novel antiproliferative spiroisoxazoline compounds using docking studies, Iranian Journal of Pharmaceutical Research, 14(1):141-147.

(Continued)

*Primary Examiner* — Rei Tsang Shiao
(74) *Attorney, Agent, or Firm* — Knobbe, Martens, Olson & Bear, LLP

(57) ABSTRACT

Disclosed herein are compositions including a compound of formula (I) for treating cancer. Some embodiments relate to methods of treating cancer by co-administering a compound of formula (I) and one or more immune checkpoint inhibitor to a subject in need thereof. Some embodiments relate to methods of treating cancer by co-administering a compound of formula (I) and plinabulin to a subject in need thereof. Some embodiments relate to methods of providing co-stimulation of T-cell activation against cancer by co-administering a compound of formula (I), one or more immune checkpoint inhibitor.

26 Claims, 4 Drawing Sheets

(56) References Cited

U.S. PATENT DOCUMENTS

| | | |
|---|---|---|
| 8,129,527 B2 | 3/2012 | Palladino et al. |
| 8,168,757 B2 | 5/2012 | Finnefrock et al. |
| 8,217,149 B2 | 7/2012 | Irving et al. |
| 8,247,552 B2 | 8/2012 | Palladino et al. |
| 8,618,292 B2 | 12/2013 | Palladino et al. |
| 9,358,289 B2 | 6/2016 | Korman et al. |
| 9,394,368 B2 | 7/2016 | Brogdon et al. |
| 10,076,518 B2 | 9/2018 | Huang |
| 10,155,748 B2 | 12/2018 | Huang et al. |
| 10,238,650 B2 | 3/2019 | Huang |
| 10,357,491 B2 | 7/2019 | Huang |
| 10,550,104 B2 | 2/2020 | Huang et al. |
| 10,569,169 B2 | 2/2020 | Li et al. |
| 10,596,169 B2 | 3/2020 | Huang |
| 10,668,063 B2 | 6/2020 | Huang |
| 10,912,748 B2 | 2/2021 | Mohanlal |
| 2002/0028819 A1 | 3/2002 | Teng et al. |
| 2002/0143021 A1 | 10/2002 | Fukumoto et al. |
| 2004/0102454 A1 | 5/2004 | Hayashi et al. |
| 2004/0176372 A1 | 9/2004 | Suto et al. |
| 2006/0079534 A1 | 4/2006 | Kanzaki et al. |
| 2006/0167010 A1 | 7/2006 | Hayashi et al. |
| 2006/0223822 A1 | 10/2006 | Hayashi et al. |
| 2007/0293453 A1 | 12/2007 | Fisher et al. |
| 2008/0199485 A1 | 8/2008 | Kundig et al. |
| 2008/0255035 A1 | 10/2008 | Trieu et al. |
| 2009/0170837 A1 | 7/2009 | Gourdeau et al. |
| 2009/0317368 A1 | 12/2009 | Chen |
| 2012/0041070 A1 | 2/2012 | Shengfan et al. |
| 2012/0277251 A1 | 11/2012 | Palladino et al. |
| 2013/0131018 A1 | 5/2013 | Leblond et al. |
| 2013/0303481 A1 | 11/2013 | Marcus |
| 2014/0322275 A1 | 10/2014 | Brogdon et al. |
| 2015/0202291 A1 | 7/2015 | Bosch et al. |
| 2015/0291549 A1 | 10/2015 | Chupak et al. |
| 2016/0243153 A1 | 8/2016 | Sundaram et al. |
| 2017/0226221 A1* | 8/2017 | Madiyalakan .......... A61P 37/02 |
| 2018/0028531 A1 | 2/2018 | Huang et al. |
| 2018/0140600 A1 | 5/2018 | Li et al. |
| 2019/0175587 A1 | 6/2019 | Huang et al. |
| 2019/0209549 A1 | 7/2019 | Arline et al. |
| 2020/0038395 A1 | 2/2020 | Mohanlal |
| 2020/0129504 A1 | 4/2020 | Mohanlal et al. |
| 2020/0237754 A1 | 7/2020 | Huang |
| 2020/0277280 A1 | 9/2020 | Huang |
| 2020/0281921 A1 | 9/2020 | Huang |
| 2020/0289503 A1 | 9/2020 | Huang |
| 2021/0030843 A1 | 2/2021 | Mohanlal |
| 2021/0046068 A1 | 2/2021 | Huang |
| 2021/0161888 A1 | 6/2021 | Huang et al. |
| 2021/0177952 A1 | 6/2021 | Mohanlal et al. |
| 2021/0275524 A1 | 9/2021 | Huang |
| 2022/0378784 A1 | 12/2022 | Mohanlal et al. |
| 2022/0387365 A1 | 12/2022 | He |
| 2023/0035763 A1 | 2/2023 | Tonra |

FOREIGN PATENT DOCUMENTS

| | | |
|---|---|---|
| EA | 016817 B1 | 7/2012 |
| EP | 0 054 924 | 6/1982 |
| EP | 0 655 060 | 1/1998 |
| GB | 2143823 | 2/1985 |
| JP | 05-9164 | 1/1993 |
| JP | 05-255106 | 10/1993 |
| JP | 10-130266 | 5/1998 |
| JP | 2002-507612 A | 3/2002 |
| JP | 2012-144512 | 8/2012 |
| JP | 2013-501791 | 1/2013 |
| JP | 2016-516523 | 6/2016 |
| RU | 2258702 | 8/2005 |
| RU | 2011 148 945 A | 4/2010 |
| WO | WO 87/05297 | 9/1987 |
| WO | WO 94/07479 | 4/1994 |
| WO | WO 95/06077 | 3/1995 |
| WO | WO 95/21832 | 8/1995 |
| WO | WO 96/20190 | 7/1996 |
| WO | WO 99/38844 | 8/1999 |
| WO | WO 99/048889 | 9/1999 |
| WO | WO 00/012121 | 3/2000 |
| WO | WO 01/053290 | 7/2001 |
| WO | WO 01/070663 | 9/2001 |
| WO | WO 03/074550 | 9/2003 |
| WO | WO 03/097164 | 11/2003 |
| WO | WO 04/016600 | 2/2004 |
| WO | WO 04/054498 | 7/2004 |
| WO | WO 04/093831 | 11/2004 |
| WO | WO 05/077940 | 8/2005 |
| WO | WO 06/121168 | 11/2006 |
| WO | WO 07/035841 | 3/2007 |
| WO | WO 07/113648 | 10/2007 |
| WO | WO 08/128169 | 10/2008 |
| WO | WO 09/089260 | 7/2009 |
| WO | WO 10/001169 | 1/2010 |
| WO | WO 10/083439 | 7/2010 |
| WO | WO 11/034954 | 3/2011 |
| WO | WO 11/050344 | 5/2011 |
| WO | WO 11/066389 | 6/2011 |
| WO | WO 11/079507 | 7/2011 |
| WO | WO 11/109625 | 9/2011 |
| WO | WO 11/146382 | 11/2011 |
| WO | WO 11/151423 | 12/2011 |
| WO | WO 12/014549 | 2/2012 |
| WO | WO 12/035436 | 3/2012 |
| WO | WO 12/074904 | 6/2012 |
| WO | WO 12/145493 | 10/2012 |
| WO | WO 13/078537 | 6/2013 |
| WO | WO 13/090552 | 6/2013 |
| WO | WO 13/177633 | 12/2013 |
| WO | WO 14/066834 | 5/2014 |
| WO | WO 14/130657 | 8/2014 |
| WO | WO 14/160183 | 10/2014 |
| WO | WO 14/195852 | 12/2014 |
| WO | WO 15/069770 | 5/2015 |
| WO | WO 15/069790 | 5/2015 |
| WO | WO 15/160641 | 10/2015 |
| WO | WO 16/081281 | 5/2016 |
| WO | WO 16/165007 | 10/2016 |
| WO | WO 17/062505 | 4/2017 |
| WO | WO 18/129381 | 7/2018 |
| WO | WO 19/194738 | 10/2019 |
| WO | WO 21/225908 | 11/2021 |

OTHER PUBLICATIONS

Abstracts of The 1999 Joint Chubu and Kansai Branch Conference and Symposia of Japan Society for Bioscience, Biotechnology, and Agrochemistry, (1999) p. 48.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

Agarwal et al., "OP449, a Novel SET Antagonist, Is Cytotoxic To Leukemia Cells and Enhances Efficacy of Tyrosine Kinase Inhibitors in Drug-Resistant Myeloid Leukemias," pursuant to an EMBASE record for a Conference ABSTRACT: 603. Oncogenes and Tumor Suppressors: Poster II (Nov. 15, 2013) Blood (2013) 122(21): 2511.

Aggarwal et al., Antiangiogenic agents in the management of non-small cell lung cancer: Where do we stand now and where are we headed? Cancer Biology & Therapy (2012), 13(5), 247-263.

Ahmed et al. "A new rapid and simple non-radioactive assay to monitor and determine the proliferation of lymphocytes: an alternative to [$^3$H]thymidine incorporation assay." J. Immunol. Methods. 170, 211-224 (1994).

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48: 235-41.

Asahina, T., "Spectrochemical Study of Amino-acid Anhydrides," Bulletin of the Chemical Society of Japan, (1930) 5, 354-365.

(56) References Cited

OTHER PUBLICATIONS

Augustin, M. "Die Umsetzung des 2,5-Diketopiperazins mit Aldehyden und Nitrosoverbindungen" Journal für Praktische Chemie, (1966) 32(4), 158-166.

Aviel-Ronen et al., "K-ras Mutations in Non-Small-Cell Lung Carcinoma: A Review," Clinical Lung Cancer (Jul. 2006) vol. 8, No. 1, pp. 30-38.

Bankowska et al., Derivatives of 1,2,3-triazole. Potential drugs?, Wiadomosci Chemiczne (2012), 66(11-12), 993-1022.

Beavis et al., "Dual PD-1 and CTLA-4 Checkpoint Blockade Promotes Antitumor Immune Responses through $CD4^+Foxp^{3I}$ -Cell-Mediated Modulation of $CD103^+$Dendritic Cells," Cancer Immunol Res (Sep. 2018) 6(9):1069-1081.

Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.

Bertelsen et al., "Vascular effects of plinabulin (NPI-2358) and the influence on tumour response when given alone or combined with radiation," International Journal of Radiation Biology (2011),87(11), 1126-1134.

Bertino J., et al., "Principles of Cancer Therapy." Cecil Textbook of Medicine. Eds. Lee Goldman, et al. 21nd ed., (2000), Chapter 198, pp. 1060-1074.

Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508.

Bond et al. "The Synthesis of Viridamine, a Penicillium Viridicatum Mycotoxin." Synthetic Commun. 19 (13&14), 2551-2566 (1989).

Borisy, G.G. "A Rapid Method for Quantitative Determination of Microtubule Protein using DEAE- Cellulose Filters." Anal. Biochem. 50, 373-385 (1972).

Braga et al. "Crystal Polymorphism and Multiple Crystal Forms," Struct Bond (2009) 132:25-50.

Brahmer et al., "Safety and Activity of Anti-PD-L1 Antibody in Patients with Advanced Cancer," N Engl J Med (2012) 366:2455-2465.

Burtles, Sally, "Transition from Preclinical to first-in-man Phase", Expert Scientific Group on Phase One Clinical Trials Final Report, Presentation Jun. 19, 2006, pp. 35-38.

Cai, Small molecule vascular disrupting agents: potential new drugs for cancer treatment, a 2009 update, Frontiers in Anti-Cancer Drug Discovery (2010), 1, 380-427.

Cai, Sui X., "Small Molecule Vascular Disrupting Agents: Potential New Drugs for Cancer Treatment", Recent Pat Anticancer Drug Discov. (2007) 2(1): 79-101.

Caira, 1998, Crystalline polymorphism of organic compounds, Topics in Current Chemistry, 198:163-208.

Callahan et al., "At the Bedside: CTLA-4- and PD-1-blocking antibodies in cancer immunotherapy", J Leukocyte Biol, vol. 94, Jul. 2013, pp. 41-53.

Carter et al., "No patient left behind: The promise of immune priming with epigenetic agents," Oncoimmunology (2017) vol. 6, No. 10, e1315486 (13 pages).

Chaplin et al., "Antivascular approaches to solid tumour thereapy: evaluation of tubulin binding agents", Br. J. Cancer 1996, 74 (Suppl. XXVII), S86-S88.

Chen et al., "Adjuvant effect of docetaxel on the immune responses to influenza A H1N1 vaccine in mice," BMC Immunology (2012) 13:36, pp. 1-12.

Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.

ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltrials.gov/ct2/show/NCT00892931> 7 pages.

ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019]. <URL: https://clinicaltrials.gov/ct2/show/NCT02846792?term=plinabuilin&rank=1> 11 pages.

Cole, P., "Durvalumab, Human anti-PD-L1 monoclonal antibody Immune checkpoint inhibitor Oncolytic", Drugs of the Future 2014, 39(12): pp. 843-847.

Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.

Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.

Cui et al. "Novel Mammalian Cell Cycle Inhibitors, Tryprostatins A, B and Other Diketopiperazines Produced by Aspergillus fumigatus." J. Antibiotics. 49(6), 534-40 (1996).

Cui et al. "Novel Mammalian Cell Cycle Inhibitors, Tryprostatins A, B and Other Diketopiperazines Produced by Aspergillus fumigatus." J. Antibiotics. 49(6): 527-33 (1996).

Davis et al., ZD6126: A Novel Vascular-targeting Agent That Causes Selective Destruction of Tumor Vasculature, Cancer Research (Dec. 15, 2002) 62: 7247-7253.

Dörwald, F., "Side Reactions in Organic Synthesis" Wiley-VCH Verlag GmbH & Co. KgaA, Weinheim, (2005), book cover and preface p. IX only.

Drug Approval And Licensing Procedures in Japan 2001, 2001, pp. 243-244.

Dunitz et al., "Disappearing Polymorphs," Acc. Chem. Res. (1995) vol. 28, No. 4, pp. 193-200.

Fernandez-Medarde et al., Mar. 2011, Ras in cancer and developmental diseases, Genes & Cancer, 2(3):344-358.

Ferrer et al., Plinabulin: tubulin polymerization inhibitor vascular-disrupting agent oncolytic, Drugs of the Future (2010), 35(1), 11-15.

Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.

Frost et al., Novel Syngeneic Pseudo-orthotopic Prostate Cancer Model: Vascular, Mitotic and Apoptotic Responses to Castration, Microvasc Research (Dec. 2004) 69: 1-9.

Fukushima et al., "Biological Activities of Albonoursin," J. Antibiotics, (1973) 26:175.

Gallina et al., "Condensation of 1,4-diacetylpiperazine-2,5-dione with aldehydes", Tetrahedron 1974, 30, 667-673.

Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.

Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).

Goldani et al. "Treatment of murine pulmonary mucormycosis with SCH 42427, a broad-spectrum triazole antifungal drug", Correspondence, J Antimicrob Chemother. 33, 369-372 (1994).

Goldfarb et al., "Synthesis of β-2-thienylalanine," Izvestiya Akademii Nauk SSSR, Seriya Khimicheskaya, (1958) 98-100, as abstracted by CAPLUS.

Gordon et al. "Reductive Alkylation on a Solid Phase: Synthesis of a Piperazinedione Combinatorial Library." J. Bioorg. Med. Chem. Letters. 5, 47-50 (1995).

Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4): 1021-1025.

Gridelli et al., Vascular disrupting agents: a novel mechanism of action in the battle against non-small cell lung cancer, Oncologist (2009), 14(6), 612-620.

Gu et al., "Identification of CTLA-4 isoforms produced by alternative splicing and their association with myasthenia gravis," Clinical Immunology (Sep. 2008) vol. 128, Issue 3, pp. 374-381.

Gura, Trisha, "Cancer Models: Systems for Identifying New Drugs are Often Faulty", Science 7(Nov. 1997) 278(5340): 1041-1042.

(56) References Cited

OTHER PUBLICATIONS

Hamel, E. "Antimitotic Natural Products and Their Interactions with Tubulin." Med. Res. Rev. (1996) 16(2): 207-31.

Hartwell et al. "Checkpoints: Controls that Ensure the Order of Cell Cycle Events." Science. 246, 629-34 (1989).

Hayakawa, Structure-activity relationship analysis, Japnaese Journal of Cancer and Chemotherapy, (2004), 31(4):526-528.

Hayashi et al., "Total Synthesis of Anti-microtubule Diketopiperazine Derivatives: Phenylahistin and Aurantiamine," J. Org. Chem., (2000) 65: 8402-8405.

Hayashi et al., Medicinal chemistry and chemical biology of diketopiperazine-type antimicrotubule and vascular-disrupting agents, Chemical & Pharmaceutical Bulletin (2013), 61(9), 889-901.

Hayashi et al., Small peptide-based medicinal chemistry for intractable disease, Peptide Science (2009), vol. Date 2008, 45th, 139-140.

He et al., "Low-dose paclitaxel enhances the anti-tumor efficacy of GM-CSF surface-modified whole- tumor-cell vaccine in mouse model of prostate cancer," Cancer Immunology Immunotherapy (2011) vol. 60, No. 5, pp. 715-730. Abstract.

Heist et al., "Abstract C30: Phase 1/2 study of the vascular disrupting agent (VCA) plinabulin (NPI- 2358) combined with docetaxel in patients with non-small cell lung cancer (NSCLC)," *Mol. Cancer Ther*., 2009; 8(12 Suppl):C30, 2 pages.

Heist et al., "Randomized Phase 2 Trial of Plinabulin (NPI-2358) Plus Docetaxel in Patients with Advanced Non-Small Lung Cancer (NSCLC)," 2014 ASCO Annual Meeting. . (abstr 8054) Poster Presentation. Retrieved from the internet Jul. 17, 2017: <http://meetinglibrary.asco.org/record/92548/poster>.

Heist et al., "Randomized phase 2 trial of plinabulin (NPI-2358) plus docetaxel in patients with advanced non-small cell lung cancer (NSCLC)." J. Clin. Oncol. (2014) vol. 32, No. 5s, (suppl; abstr 8054).

Helleman et al. "The International Journal of Biochemistry & Cell Biology," vol. 42, pp. 25-30 (2010).

Horak et al. "Structures of the Austalides A-E, Five Novel Toxic Metabolites from Aspergillus ustus." J Chem Soc Chem Commun. (1981) 1265-67.

http://scienceandresearch.homeoffice.gov.uk/animal-research/publications-and-reference/001-abstracts/abstracts2-2006/02november-2006/4577view=Html; "Abstract #457, Animals in Scientific Procedures (2006)"; (accessed on Nov. 19, 2008).

Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.

Hyun et al., "Valine dehydrogenase from Streptomyces albus: gene cloning, heterologous expression and identification of active site by site-directed mutagenesis," FEMS Microbiology Letters (Jan. 1, 2000) 182: 29-34.

Iwasaki, S. "Antimitotic Agents: Chemistry and Recognition of Tubulin Molecule." Med Res Rev. (1993) 13: 183-198.

Iwasaki, S. "Bioactive Natural Products Interfering with Microtubule Function." Kagaku to Seibutsu. 32(3): 153-159 (1994).

Ji et al., Tubulin Colchicine Binding Site Inhibitors as Vascular Disrupting Agents in Clinical Developments, Current Medicinal Chemistry (2015), 22(11), 1348-1360.

Jiang et al., "A Novel Peptide Isolated from a Phage Display Peptide Library with Trastuzumab Can Mimic Antigen Epitope of HER-2*," (Feb. 11, 2005) J Biol Chem, vol. 280, No. 6, pp. 4656-4662.

Johnson et al. "Kinetic Analysis of Microtubule Self-assembly in Vitro." J. Mol. Biol. 117, 1-31 (1977).

Jure-Kunkel M. et al., "Synergy between chemotherapeutic agents and CTLA-4 blockade in preclinical tumor models", Cancer Immunol. Immunother. 2013, vol. 62, pp. 1533-1545.

Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.

Kamb, Alexander, "What's wrong with our cancer models?", Nature Reviews Drug Discovery (Feb. 2005) 4: 161-165.

Kanoh et al., "(−)-Phenylahistin: A New Mammalian Cell Cycle Inhibitor Produced by Aspergillus USTUS," Bioorganic & Medicinal Chemistry Letters, (1997) 7: 2847-2852.

Kanoh et al., "(−)-Phenylahistin Arrests Cells in Mitosis by Inhibiting Tubulin Polymerization," The Journal of Antibiotics, (1999) 52: 134-141.

Kanoh et al., "Antitumor Activity of Phenylahistin in Vitro and in Vivo," Bioscience Biotechnology Biochemistry, (1999) 63(6): 1130-1133.

Kanoh et al., "Synthesis and Biological Activities of Phenylahistin Derivatives," Bioorganic & Medicinal Chemistry, (1999) 7: 1451-1457.

Kanthou et al., Microtubule depolymerizing vascular disrupting agents: novel therapeutic agents for oncology and other pathologies, International Journal of Experimental Pathology(2009), 90(3), 284-294.

Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12):1042-1047.

Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.

Kanzaki et al., "Effective Production of Dehydro Cyclic Dipeptide Albonoursin Exhibiting Pronuclear Fusion Inhibitory Activity, II. Biosynthetic and Bioconversion Studies," The Journal of Antibiotics, (2000) 53(1): 58-62.

Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.

Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).

Kanzaki et al., "Novel Cyclic Dipeptide Dehydrogenase and Assay Method for Its Activity," Scientific Reports of the Faculty of Agriculture, Okayama University, (1999) 88: 7-11.

Keepers et al. "Comparison of the Sulforhodamine B Protein and Tetrazolium (MTT) Assays for in vitro Chemosensitivity Testing." Eur. J. Cancer. 27, 897-900 (1991).

Kim et al. "Polymer attached cyclic peptides, tetrahedron: Asymmetry." 3(11):1421-1430 (1992).

Kingston, Correction to Tubulin-interactive natural products as anticancer agents, Journal of Natural Products (2011), 74(5), 1352.

Kingston, Tubulin-Interactive Natural Products as Anticancer Agents, Journal of Natural Products (2009), 72(3), 507-515.

Kobayashi et al., "Microtubule Assembly Regulators of Microbial Origin," Abstract of Paper Read at the 1989 Symposium on the Chemistry of Natural Products, (1989) 51.

Kola et al., "Can the pharmaceutical industry reduce attrition rates?", Nature Reviews Drug Discovery (2004) 3: 711-715.

Kondoh et al. "Effects of Tryprostatin Derivatives on Microtubule Assembly In Viro and In Situ." J. Antibiotics. 51, 801-04 (1998).

Kopple et al., "A Convenient Synthesis of 2,5-Piperazinediones1a," The Journal of Organic Chemistry, (1967) 33: 862-864.

Kreamer K., "Immune checkpoint blockade: A New Paradigm in Treating Advanced Cancer", J. Adv. Pract. Oncol., 2014, vol. 5, pp. 418-431.

Krishan, A. "Rapid Flow Cytofluorometric Analysis of Mammalian Cell Cycle By Propidium Iodide Staining." J. Cell Biol. 66, 188-193 (1975).

Kupchan et al. "Steganacin and Steganangin, Novel Antileukemic Lignan Lactones from Steganotaenia araliacea 1-3." J. Am. Chem. Soc. (1973) 95(4): 1335-36.

Küster & Koeppenhöfer, "Über eininge Pyrrolderivate," Z. Physiol, Chem., (1927) 172:126-137.

Lacey et al. "Interaction of Phomopsin A and Related Compounds with Purified Sheep Brain Tubulin." Biochem. Pharmacol. 36, 2133-38 (1987).

(56) References Cited

OTHER PUBLICATIONS

Laemmli, U.K. "Cleavage of Structural Proteins during the Assembly of the Head of Bacteriophage T4." Nature. 227, 680-85 (1970).
Larsen et al. "Aurantiamine, A Kiketopiperazine from Two Varieties of Penicillium Aurantiogriseum." Phytochemistry. 31, 1613-1615 (1992).
Leaf, Clifton, "Why are we losing the war on cancer (And how to win it)?", Health Administrator (2005) XVII(1): 172-183.
Lee et al. "The Reconstitution of Microtubules from Purified Calf Brain Tubulin." Biochemistr. 14(23), 5183-87 (1975).
Lee et al., "A practical guide to pharmaceutical polymorph screening & selection," Asian Journal of Pharmaceutical Sciences (2014) vol. 9, pp. 163-175.
Lee et al., Colchicine site inhibitors of microtubule integrity as vascular disrupting agents, Drug Development Research (2008), 69(6), 352-358.
Li. Y., et al. "Interaction of marine toxin dolastatin 10 with porcine brain tubulin: competitive inhibition of rhizoxin and phomopsin A binding." Chem. Biol. Interact. 93, 175-83 (1994).
Liao et al., "Design and synthesis of novel soluble 2,5-diketopiperazine derivatives as potential anticancer agents," European J Med Chem (2014) 83:236-244.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicial Chemstry, 47(17):4247-4257.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Lu et al., Nov. 2012, An overview of tubulin inhibitors that interact with the colchicine binding site, Pharmaceutical Research, 29(11):2943-2971.
Luduena, R.F. "Contrasting Roles of Tau and Microtubule-associated Protein 2 in the Vinblastine-induced Aggregation of Brain Tubulin." J. Biol. Chem. 259:12890-98 (1984).
Lyman et al., "Risk Models for Predicting Chemotherapy-Induced Neutropenia," The Oncologist (2005) 10:427-437.
Lynch et al., "Ipilimumab in Combination With Paclitaxel and Carboplatin As First-Line Treatment in Stage IIIB/IV Non-Small-Cell Lung Cancer: Results From a Randomized, Double-Blind, Multicenter Phase II Study." (Jun. 10, 2012) J Clin Oncol, vol. 30, No. 17, pp. 2046-2054.
Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.
Mita et al., "Phase 1 First-in-Human Trial of the Vascular Disrupting Agent Plinabulin (NPI-2358) in Patients with Solid Tumors or Lymphomas," *Clinical Cancer Research* (2010), 16(23), 5892-5899.
Mita et al., "Phase II study of docetaxel with or without plinabulin (NPI-2358) in patients with non-small cell lung cancer (NSCLC)", *J. Clin. Oncol.*, 2010, vol. 28, No. 15 supplement. Abstract 7592, 2 pages.
Mita et al., Randomized Phase 2 Study of Docetaxel +/− Plinabulin (NPI-2358) in Patients with Non-Small Cell Lung Cancer (NSCLC), *Poster Presentation at ACS Annual '10 Meeting* (Jun. 4-8, 2010) 1 page.
Mitsudomi et al., "Mutations of ras genes distinguish a subset of non-small-cell lung cancer cell lines from small-cell lung cancer cell lines," *Oncogene* (Aug. 1991) vol. 6, No. 8, pp. 1352-1362.
Mohanlal et al., "The plinabulin/docetaxel combination to mitigate the known safety concerns of docetaxel," J Clin Oncol (2016) 34(15_suppl), Abstract e20595.
Muguruma et al., OP-20: "Application of Fc-selective Z33-peptide to the preparation of non-covalent- type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 In English (Oral Presentation). Abstract.
Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," NEOPLASIA (Aug. 2013) vol. 15, No. 8, pp. 939-951.
Neidle, Stephen, ed., Cancer Drug Design and Discovery, 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), Volume Date 2006, 17(1), 25-31.
Niemann et al, "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Ohaegbulam et al., "Human cancer immunotherapy with antibodies to the PD-1 and PD-L1 pathway," Trends Mol Med, (Oct. 30, 2014) 21(1): pp. 24-33.
Ott et al., "CTLA-4 and PD-1/PD-L1 Blockade: New Immunotherapeutic Modalities with Durable Clinical Benefit in Melanoma Patients," Clin Cancer Res (Oct. 1, 2013) 19(19): pp. 5300-5309.
Paik et al., "A Phase 2 Study of Weekly Albumin-Bound Paclitaxel (Abraxane@) Given as a Two-Hour Infusion", Cancer Chemother. Pharmacol., Nov. 2011, vol. 68, No. 5, pp. 1331-1337.
Pardoll et al., "The blockade of immune checkpoints in cancer immunotherapy," Nat Rev Cancer (May 4, 2016) 12(4): 252-264.
Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, pp. 16667-16674.
Perez, Edith A., "Paclitaxel in Breast Cancer," *The Oncologist*, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.

(56) References Cited

OTHER PUBLICATIONS

Prior et al., "A Comprehensive Survey of Ras Mutations in Cancer" Cancer Res. (2012) vol. 72, No. 10, pp. 2457-2467.
Raza et al., 2014, Polymorphism: the phenomenon affecting the performance of drugs, SOJ Pharmacy & Pharmaceutical Sciences, 10 pp.
Reck, M., "What future opportunities may immuno-oncology provide for improving the treatment of patients with lung cancer?" (2012) Annals of Oncology (Sep. 2012) 23 (Supp. 8) viii28-viii34.
Remington, "The Science and Practice of Pharmacy, 20th Ed" (2000) p. 709.
Rhodes, John, "Section Review: Biologicals & Immunologicals: Therapeutic potential of Schiff base- forming drugs," Expert Opinion on Investigational Drugs (1996) vol. 5, Issue 3, pp. 257-268.
Riemer et al., "Matching of trastuzumab (Herceptin®) epitope mimics onto the surface of Her-2/neu—a new method of epitope definition," Mol Immunol 42 (2005) pp. 1121-1124.
Roberge et al., "Antitumor Drug Fostriecin Inhibits the Mitotic Entry Checkpoint and Protein Phospatases 1 and 2A." Cancer Res. 54, 6115-21 (1994).
Roberts et al, "Trends in the Risks and Benefits to Patients with Cancer Participating in Phase 12 Clinical Trials", JAMA (2004) 292(17): 2130-2140.
Rowinsky et al, "The clinical pharmacology and use of antimicrotubule agents in cancer chemotherapeutics", Pharmacol. Ther. 1991, 52, 35-84.
Rowinsky et al. "Taxol: A Novel Investigational Antimicrotubule Agent." J. Natl. Cancer Inst. 82(15): 1247-59 (1990).
Rozali et al., "Programmed Death Ligand 2 in Cancer-Induced Immune Suppression," Clinical and Developmental Immunology (2012) Article ID 656340, pp. 1-8.
Sackett, D.L. "Podophyllotoxin, Steganacin and Combretastatin: Natural Products that Bind at the Colchicine Site of Tubulin." Pharmacol. Ther. (1993) 59: 163-228.
Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.
Scholl et al., "Synthetic Lethal Interaction between Oncogenic KRAS Dependency and the STK33 Suppression in Human Cancer Cells", Cell (May 29, 2009) 137 pp. 821-834.
Sele et al., Jul. 2016, Novel 4-(pyrimidin-2-yl)morpholines targeting the colchicine-binding site of tubuline, Cancer Research, 76(14):abstract.
Sezaki et al., "Drug Delivery Systems", Drug Development, (Jul. 1989) 13: 116, Table 2. 29.
Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.
Shen et al., Time- and dose-dependent vascular changes induced by the novel vascular disrupting drug NPI-2358 in a murine cancer model monitored with DCE-MRI, U.S. Chinese Journal of Lymphology and Oncology(2010), 9(4), 151-153.
Sherline et al. "Binding of Colchicine to Purifiied Microtubule Protein." J. Biol. Chem. 250, 5481-86 (1975).
Shi, Q et al, "Recent progress in the development of tubulin inhibitors as antimitotic antitumor agents", Curr. Pharm. Des. 1998, 4, 219-248.
Singh et al., "A novel vascular disrupting agent plinabulin triggers JNK-mediated apoptosis and inhibits angiogenesis in multiple myeloma cells," Blood (2011), 117(21), 5692-5700.
Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.
Smedsgaard et al. "Using direct electrospray mass spectrometry in taxonomy and secondary metabolite profiling of crude fungal extracts." J. Microbiol. Meth. (1996) 25: 5-17.
Sölter et al., Barettin, Revisited? Tetrahed Lttrs. (Mar. 2002) 43: 3385-3386.
Spear et al., Vascular disrupting agents (VDA) in oncology: advancing towards new therapeutic paradigms in the clinic, Current Drug Targets (2011), 12(14), 2009-2015.
Stein, J., ed. "Internal Medicine," Fourth Edition, Mosby-Year Book, Inc., (1994), Chapters 71-72, pp. 699-729.
Stenehjem et al., "PDI/PDLI inhibitors for the treatment of advanced urothelial bladder cancer," OncoTargets and Therapy (2018) 11:5973-5989.
Steyn, P.S. "The Structures of Five Diketopiperazines from Aspergillus Ustus." Tetrahedron. 29, 107-120 (1973).
Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).
Takahashi et al. "Rhizoxin binding to tubulin at the maytansine-binding site." Biochim. Biophys. Acta. 926, 215-23 (1987).
Talmadge et al., Murine models to evaluate novel and conventional therapeutic strategies for cancer., Am J Pathol, 2007, vol. 170, Issue 3, pp. 793-804.
Thorpe, Philip E., "Vascular Targeting Agents as Cancer Therapeutics," Clinical Cancer Research, vol. 10, 415-427, Jan. 15, 2004.
Tiwari et al. "A pH- and Temperature-Dependent Cycling Method that doubles the Yield of Microtubule Protein." Anal. Biochem. 215, 96-103 (1993).
Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.
Topalian et al., "Safety, Activity, and Immune Correlates of Anti-PD-1 Antibody in Cancer," N Engl J Med. (Jun. 28, 2012) 366(26):2443-2454.
Tozer et al., Tumour vascular disrupting agents: combating treatment Resistance, British Journal of Radiology (2008), 81(Spec. Iss. 1), S12-S20.
Turner et al. "Recent Advances in the Medicinal Chemistry of Antifungal Agents." Current Pharmaceutical Design. 2, 209-224 (1996).
US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.
Usui et al. "Tryprostatin A, a specific and novel inhibitor of microtubule assembly." Biochem J. 333, 543-48 (1998).
Van der Waerden, B.L., "Wirksamkeits—und Konzentrationsbestimmung durch Tierversuche." Arch Exp Pathol Pharmakol. 195, 389-412, (1940).
Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).
Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.
Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.
Wang, Y. et al., "Structures of a diverse set of colchicine binding site inhibitors in complex with tubulin provide a rationale for drug discovery." FEBS Journal (2016) 283, 102-111.
Weisenberg et al. "The Colchicine-Binding Protein of Mammalian Brain and its Relation to Microtubules." Biochemistry (1968) 7(12): 4466-79.
Wilt et al. "Anal cancer in Alaska; a retrospective study of incidence, treatment, and outcomes". Alaska Med Jul.-Sep. 2002; 44(3):56-9, 62.
Yahara et al. "Microtubule Organization of Lymphocytes and its Modulation by Patch and Cap Formation." Cell. 15, 251-259 (1978).
Yamato et al., "Clinical importance of B7-H3 expression in human pancreatic cancer," British Journal of Cancer (Oct. 20, 2009) 101, pp. 1709-1716.

(56) References Cited

OTHER PUBLICATIONS

Yamazaki et al. "Crystal Structure and Absolute Configuration of Fumitremorgin B, a Tremorgenic Toxin from Aspergillus Fumigatus Fres." Tetrahedron Lett. 1, 27-28 (1975).
Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.
Yamazaki et al., Drug discovery study on cyclic dipeptides anticancer drugs and chemical biological development, Idenshi Igaku Mook (2012), 21(Saishin Pepuchido Gosei Gijutsu to Sono Soyaku Kenkyu eno Oyo), 260-266.
Yamori T., "A Human Cell Line Panel for Screening Anti-Cancer Drugs", Jap. J. Cancer Chemother. 24, 129-35 (1997).
Yang et al., "The KRAS Mutation is Highly Correlated With EGFR Alterations in Patients With Non-small Cell Lung Cancer," Fooyin J Health Sci (2009) vol. 1(2): pp. 65-71.
Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, P2.01-087.
Yin et al., "Human Mutations That Confer Paclitaxel Resistance," Mol. Cancer Ther. vol. 9(2), pp. 327-335 (2010).
Yokio et al, "Neihumicin, A New Cytotoxic Antibiotic From Micromonospora Neihuensis," The Journal of Antibiotics, (Apr. 1988) 41(4):494-501.
Yoshida, M.M. Protein Nucleic Acid Enzymes. 38, 1753-1765 (1993).
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Younis et al., 2011, The cost-utility of adjuvant chemotherapy using docetaxel and cylophosphamide compared with doxorubicin and cyclophosphamide in breast cancer, Current Oncology 18(8):e298-3296.
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.
Zheng, Lei, "Does vaccine-primed pancreatic cancer offer better candidates for immune-based therapies?" Immunotherapy (2014) 6(10):1017-1020.
Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1): 19-25.
International Search Report and Written Opinion dated May 12, 2017 in PCT/US2017/016740.
Crawford, Aug. 2003, Once=per-cycle pegilgrastim (neulata) for the managemetn of chemotherapy- induced neutrpenia, Seminars in Onocology 30(4)Suppl 13:23-30.
Dale, Oct. 2015, Neutropenia, John Wiley & Sons Ltd., www.els.net, 8 pp.
Field et al., 2014, Microtubule-targeting agents are clinically successful due to both mitotic and interphase impairment of microtubule funciton, Bioorganic & Medicinal Chemistry, 22:5050-5059.
Krendel et al., Apr. 2002, Nucelotide exchange factor GEF-H1 mediates cross-talk between microtubules and the actin cytoskeleton, Nature Cell Biology, 4:294-301 and supplementary information.
Li et al., May-Jun. 2017, Epitope mapping reveals the binding mechanism of a functional antibody cross-reactive to both human and murine programmed death 1, MABS, 9(4):628-637.
Melero et al., Aug. 2015, Evolving synergistic combinations of targeted immunotherapies to combat cancer, Nature Reviews Cancer, 15:457-472.
Mohanlal et al., Feb. 10, 2018, Plinabulin, a novel small molecule clinical stage 10 agent with anti-cancer activity, to prevent chemoinduced neutropenia and immune related AEs, Journal of Clinical Oncology, 36(5 Suppl):126.

Nabholz, 2001, Phase II study of docetaxel, doxorubiin, and cyclophosphamide as first-line chemotherapy for metastatic breast cancer, Journal of Clinical Oncology, 19:314-321.
Nielsen et al., Jun. 2005, Alternative splice variants of the human PD-1 gene, Cell Immunol., 235(2):109-116.
Rathkopf, Jun. 20, 2008, Phase II trial of docetaxel with rapid androgen cycling for progressive noncastrate prostate cancer, J. Clin. Onc. 26(18):2959-2965.
Selby et al., Sep. 9, 2016, Preclinical development of ipilimumab and nivolumab combination immunotherapy: mouse tumor models, in vitro functional studies, and cynomolgus macaque toxicology, PloS One, 11(9):e0161779, 19 pp.
Spain et al., Feb. 6, 2016, Management of toxicities of immune checkpoint inhibitors, Cancer Treatment Reviews, 44:51-60.
Vainas, 2012, Personalising docetaxel and G-CSF schedules in cancer patients by a clinically validated computational model, British J. Cancer, 107:814-822.
Wailoo, 2009, The risk of febrile neutropenia in patients with non-small-cell lung cancer treated with docetaxel: a systematic review and meta-analysis, British J. Cancer 100(3):436-441.
Buchbinder et al., Feb. 2016, CTLA-4 and PD-1 pathways: similarities, differences, and implications of their inhibition, American Journal of Clinical Oncology, 39(1):98-106.
ClinicalTrials.gov Identifier NCT03294577, "Plinabulin vs. pegfilgrastim in prevention of TAC induced neutropenia" (Sep. 27, 2107). <URL:ttps://clinicaltrials.gov/ct2/show/NCT3294577> 4 pp.
Dalgleish, 2015, Rationale for combining immunotherapy with chemotherapy, Immunotherapy, 7(3):309-316.
Das et al., Feb. 1, 2015, Combination therapy with anti-CLTA4 and antiPD1 leads to distinct immunologic changes in-vivo, J. Immunolog, 194(3):950-959.
Folkman, Dec. 2002, Role of angiogenesis in tumor growth and metastasis, Semin Oncol, 29:15-18.
Hellmann et al., Nov. 21, 2019, Nivolumab plus ipilimumab in advanced non-small-cell lung cancer, The New England Journal of Medicine, 381:2020-2031.
Hodi et al., Nov. 2016, Combined nivolumab and ipilimumab versus ipilimumab alone in patients with advanced melanoma: 2-year overall survival outcomes in a multicentre, randomised, controlled, phase 2 trial, Lancet Oncol., 17:1558-1568.
Intlekofer et al., Jul. 2013, At the bench: preclinical rationale for CTLA-4 and PD-1 blockade as cancer immunotherapy, J. Leukoc Biol., 94(1):25-39.
Kashyap et al., Sep. 24, 2019, GEF-H1 signaling upon microtubule destabilization is required for dendritic cell activation and specific anti-tumor responses, Cell Reports, 28:3367-3380.
Lloyd et al., 2015, Abstract A184: Activity of plinabulin in tumor models with kras mutations, Mol. Can. Thera. 14(12):Suppl. 2.
Natoli et al., Mar. 3, 2021. Plinabulin, a distinct microtubule-targeting chemotherapy, promotes M1-like macrophage polarization and anti-tumor immunity, Frontiers in Oncology, 11:1-14.
PRNewswire.com, Jun. 22, 2010, Nereus Pharmaceuticals completes enrollment of phase 2 advance clinical trial of plinabulin in non-small cell lung cancer, 4 pp.
Riedel et al., Jun. 2007, A phase II trial of carboplatinvinorelbine with pegfilgrastim support for the treatment of patients with advanced non-small cell lung cancer, Journal of Thoracic Oncology, 2(6):520-525.
Bauer et al., Jan. 15, 2010, Identification of markers of taxane sensitivity using proteomic and genomic analyses of breast tumors from patients receiving neoadjuvant paclitaxel and radiation, Clinical Cancer Research, 16(2):681-690.
Bazhenova, Feb. 21, 2021, Nivolumab in Combination With Plinabulin in Patients With Metastatic Non-Small Cell Lung Cancer (NSCLC), ClinicalTrials.gov, NCT02812667 version 7.
ClinicalTrials.gov, NCT00151073, Estramustine, docetaxel and zoledronate treatment in hormone-refractory adenocarcinoma of the prostate, https//clinicaltrials.gov/ct2/show/NCT00151073?term=zoledronate%2C+tubulin&draw=2&rank=1.
Collins et al., 2014, Lipid tucaresol as an adjuvant for methamphetamine vaccine development, CHemComm, 50:4079-4081.
Davies, Feb. 3, 2014, New modalities of cancer treatment for NSCLC: focus on immunotherapy, Cancer Manag. Res., 6:63-75.

(56) References Cited

OTHER PUBLICATIONS

Du et al., Jul. 2018, docetaxel increases the risk of severe infections in the treatment of non-small cell lung cancer: a meta-analysis, Oncosciene, 5(7-8):220-238.

El-Kenawi et al., Oct. 2013, Angiogenesis inhibitors in cancer therapy: mechanistic perspective on classification and treatment rationales, Br. J. Pharmacol., 170(4):712-729.

Fernandez-Tejada et al., 2014, Design, synthesis, and immunologic evaluation of vaccine adjuvant conjugates based on QS-21 and tucaresol, Bioorganic & Medicinal Chemistry, 22:5917-5923.

Fernandez-Tejada et al., 2016, Development of improved vaccine adjuvants based on the saponin natural product QS-21 through chemical synthesis, Accounts of Chemical Research 49:1741-1756.

Fessas et al., 2017, A molecular and preclinical comparison of the PC-1-targeted t-cell checkpoint inhibitors nivolumab and mebrolizumag, Seminars in Oncology, 44:136-140.

Flanigan et al., Jan. 7, 2011, Melanoma brain metastases: is it time ro reassess the bias?, Current Problems in Cancer, 35(4):200-210.

Glisson et al., 2002, Phase II trial of docetaxel and cisplatin combination chemotherapy in patients with squamous cell carcinoma of the head and neck, Journal of Clinical Oncology 20:1593-1599.

Hwang et al., 2019, Heat shock proteins: a dual carrier-adjuvant for an anti-drug vaccine against heroin, Bioorganic & Medicinal Chemistry, 27:125-132.

Ishibashi et al., Sep. 1989, Interleukin-6 is a potent thrombopoietic factor in vivo in mice, Blood, 74(4):1241-1244.

Januchowski et al., Jan. 2014, Microarray-based detection and expression analysis of extracellular matrix proteins in drug-resistant ovarian cancer cell lines, Oncology Reports, 32:1981-1990.

Journal of the Japanese Society of Internal Medicine, 2017, 106(3):534-539.

Kanojia et al., May 2015, BIII-tubulin regulates breast cancer metastes to the brain, Mol Cancer Ther., 14(5):1152-1161.

Lyman, 2011, Neutropenia, Encyclopedia of Cancer, pp. 2506-2509.

Malhotra, J., "A Phase I/II Study of Nivolumab, Ipilimumab and Plinabulin in Patients With Recurrent Small Cell Lung Cancer", ClinicalTrials.gov, NCT03575793 version 9, Apr. 15, 2020, <URL: https://clinicaltrials.gov/ct2/history/NCT03575793?V_9=View#StudyPageTop>.

Malhotra, J., Abstract 8570: "A phase I trial of plinabulin in combination with nivolumab and ipilimumab in patients with relapsed small cell lung cancer (SCLC): Big Ten Cancer Research Consortium (BTCRC-LUN17-127) study", Journal of Clinical Oncology, vol. 39, No. 15, May 28, 2021, DOI: 10.1200/JCO.2021.39.15_suppl.8570.

Mazza et al., 2017, Treating EGFR mutation resistance in non-small cell lung cancer—role of osimertinib, The Application of Clinical Genetics, 10:49-56.

Muguruma et al., 2016, Novel Hybrid Compound of a Plinabulin Prodrug with an IgG Binding Peptide for Generating a Tumor Selective Noncovalent-Type Antibody-Drug Conjugate; Bioconjugate Chem. 27(7):1606-1613.

Nereus Pharmaceuticals, Inc., Aug. 16, 2011, Phase 1/2 study of vascular disrupting agent NPI-2358+ docetaxel in patients with advanced non-small cell lung cancer, ClinicalTrials.gov, NCT00630110 <URL: https://www.clinicaltrials.gov/ct2/show/NCT00630110>.

Oxford English Dictionary Online, 2010, Definition of prevent, http://dictionary.oed.com/, 4 pp.

Plunkett et al., Aug. 1995, Gemcitabine: metabolism, mechanisms of action, and self-potentiation, Semin Oncol., 22(4 Suppl 11):3-10.

Reagan-Shaw et al., Mar. 2007, The FASEB Journal, 22:659-661.

Snegovoy Av, et al. Practical recommendations for the appointment of colony-stimulating factors in order to prevent the development of febrile neuropathy in cancer patients // Practical recommendations. Version 2016. p. 394-401.

Tsao et al., 2004, Phase I evaluation of docetaxel and topotecan for patients with advanced solid tumores, Cancer, 100:2240-2245.

Tsoumpra et al., 2015, The inhibition of human farnesyl pyrophosphate synthase by nitrogen-containing bisphosphonates. Elucidating the roles of active site threonine 201 and tyrosine 204 residues using enzyme mutants, Bone, 81:478-486.

Valet et al., Dec. 2013, Challenging single- and multi-probesets gene expression signatures of pathological complete response to neoadjuvant chemotherapy in breast cancer: experience of the REMAGUS 02 phase II trial, Breast, 22(6):1052-1059.

Vannenman et al., Mar. 22, 2012, Combining immunotherapy and targeted therapies in cancer treatment, Nat. Rev. Cancer, 12(4):237-251.

Wang et al., 2016, The D domain of LRRC4 anchors ERK1/2 in the cytoplasm and competitively inhibits MED/ERK activation in glioma cells, Journal of Hematology & Oncology, 9:130.

Weycker et al., 2019, Risk and consequences of chemotherapy-induced thrombocytopenia in US clinical practice, BMC Cancer, 19(151), 8 pp.

Zacharie et al., 1997, Regioselective synthesis of 6-substituted 2-hydroxybenzaldehyde: efficient synthesis of the immunomodulator tucaresol and related analogues, Journal of the Chemical Society, 19:2925-2929.

\* cited by examiner

COMPOSITIONS CONTAINING TUCARESOL OR ITS ANALOGS

INCORPORATION BY REFERENCE TO ANY PRIORITY APPLICATIONS

This application is a division of U.S. patent application Ser. No. 16/075,942, filed Aug. 6, 2018, which claims priority to PCT/US2017/016740, filed Feb. 6, 2017, which claim priority to U.S. Provisional Application No. 62/292,763, filed Feb. 8, 2016, the disclosure of which is incorporated herein by reference in its entirety.

BACKGROUND

Field

The present invention relates to the field of chemistry and medicine. More particularly, the present invention relates to tucaresol and its analogs, compositions containing tucaresol or its analogs, and their use in treatment.

Description of the Related Art

Human cancers harbor numerous genetic and epigenetic alterations, generating neoantigens potentially recognizable by the immune system (Sjoblom et al, 2006). The adaptive immune system, comprised of T and B lymphocytes, has powerful anti-cancer potential, with a broad capacity and exquisite specificity to respond to diverse tumor antigens.

Recent cancer immunotherapy research has focused substantial effort on approaches that enhance anti-tumor immunity by adoptive-transfer of activated effector cells, immunization against relevant antigens, providing non-specific immune-stimulatory agents such as cytokines, or removing inhibitors to anti-cancer effector cells. Efforts to develop immune modulator and specific immune checkpoint inhibitors have begun to provide new immunotherapeutic approaches for treating cancer, such as the development of an antibody, ipilimumab, that binds to and inhibits Cytotoxic T-Lymphocyte Antigen-4 (CTLA-4) for the treatment of patients with advanced melanoma (Hodi et al., 2010). In addition, nivolumab and pembrazumab, which are anti-PD-1 antibodies, have been approved for treating melanoma, NSCLC and renal cancer, but patients only had limited response to these therapies. While cancer remains as an incurable disease for the great majority of patients, there exists a particular need for developing effective therapeutic agents that can be used in cancer immunotherapy.

SUMMARY OF THE INVENTION

Some embodiments relate to a pharmaceutical composition, comprising a compound of Formula (I):

(I)

and one or more immune checkpoint inhibitor.

Some embodiments relate to a pharmaceutical composition comprising a compound of Formula (I) and plinabulin.

Some embodiments relate to a method for treating a cancer, comprising co-administering a compound of Formula (I) and one or more immune checkpoint inhibitor to a subject in need thereof.

Some embodiments relate to a method for treating a cancer, comprising co-administering a compound of Formula (I), one or more immune checkpoint inhibitor; and plinabulin to a subject in need thereof.

Some embodiments relate to a method for treating a cancer, comprising co-administering a compound of Formula (I) and plinabulin to a subject in need thereof.

In some embodiments, the compound of Formula (I) described herein is tucaresol.

DETAILED DESCRIPTION OF THE PREFERRED EMBODIMENT

Figure 1:
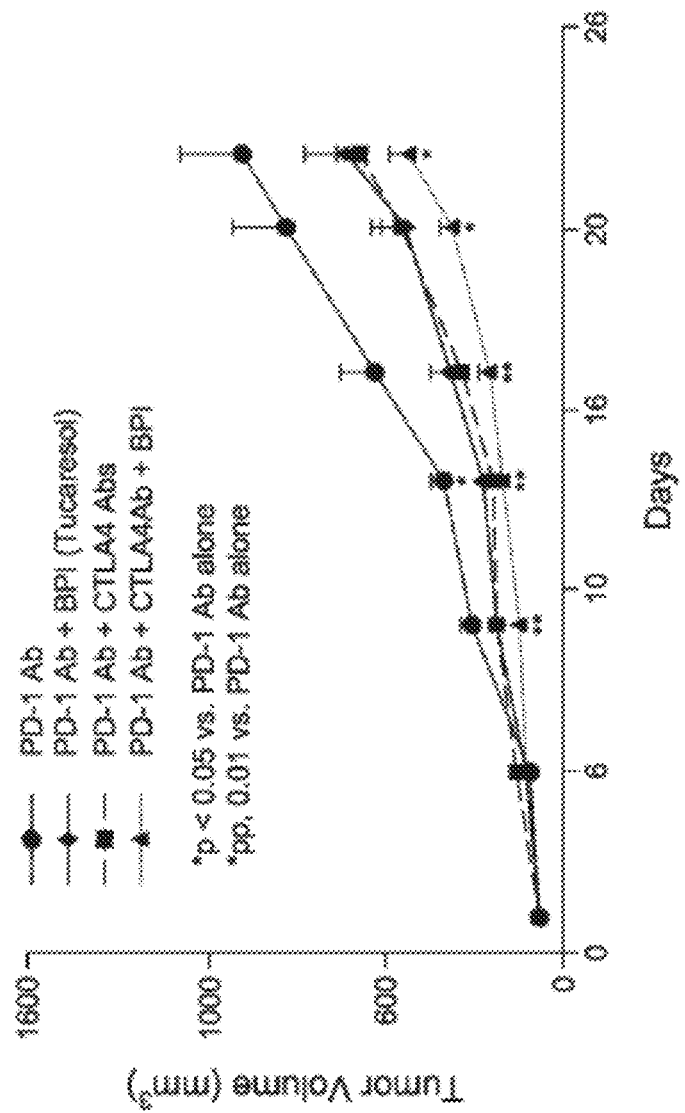
FIG. 1 shows the tumor growth in each of the four treatment groups including PD-1 antibody, PD-1 antibody/tucaresol, PD-1 and CTLA-4 antibodies, and PD-1 antibody/CTLA-4 antibody/tucaresol.

In some embodiments, compounds for use as described herein are represented by a compound of Formula (I), (I)

$Y^1$ is selected from hydroxyl, $C_{1-4}$ alkylamino and acylamino having a $C_{1-4}$ alkyl moiety thereof;

$Y^2$, $Y^3$ and $Y^4$ are independently selected from hydrogen, halogen, $C_{1-4}$ alkyl, $C_{1-4}$ alkoxy, trifluoromethyl, hydroxyl and benzyloxy; and $Q^1$ is either where $Q^2$ and $Q^3$ are independently selected from hydrogen and $C_{1-4}$ alkyl;

X is selected from cyano, carboxyl or a derivative thereof, 5-tetrazolyl and alkylsulfonylcarbamyl having a $C_{1-6}$ alkyl moiety thereof; and n is 0 or an integer selected from 1, 2, 3, 4, 5 and 6, and a pharmaceutically acceptable salt thereof.

In some embodiments, when $Y^1$ is hydroxyl, $Y^2$, 3 and $Y^4$ are all hydrogen and $Q^1$ is either

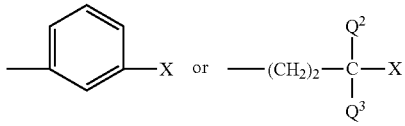

alkylsulfonylcarbamyl.

In some embodiments, the halogen for $Y^2$, $Y^3$ and $Y^4$ may be selected from iodine, bromine, chlorine and fluorine.

In some embodiments, the alkyl for $Q^2$ and $Q^3$ can independently have 1 to 2 carbon atoms (i.e. methyl or ethyl). In some embodiments, the alkyl for $Q^2$ and $Q^3$ can be methyl.

In some embodiments, X as a carboxyl derivative includes: esters, including aliphatic and aromatic hydrocarbon esters such as alkyl and aralkyl esters where for example the alkyl is $C_{1-12}$ alkyl and preferably $C_{1-4}$ alkyl (in particular methyl, ethyl, isopropyl and t-butyl) and where the aralkyl is for example benzyl; and amides, including the unsubstituted amide, N-substituted amides and N,N-disubstituted amides (embracing cyclic and heterocyclic amides) where the substituent group(s) is (are) for example aliphatic hydrocarbon such as alkyl, in particular $C_{1-6}$ alkyl such as methyl, ethyl, isopropyl and t-butyl.

In some embodiments, $Y^1$ as alkylamino can form acid addition salts. Suitable acids are well known in the art, for example hydrochloric acid and acetic acid.

In some embodiments, X is selected from cyano, 5-tetrazolyl, alkylsulfonylcarbamyl having a $C_{1-6}$ alkyl moiety thereof and a group —CO, Y, wherein Y is —$OR^1$ and $R^1$ is hydrogen, $C_{1-6}$ alkyl or benzyl, or Y is —$NR^2R^3$ where $R^2$ and $R^3$ are independently hydrogen or alkyl of 1 to 4 carbon atoms.

In some embodiments, X is carboxyl.

In some embodiments, the compound of Formula (I) is tucaresol.

Tucaresol, 4-[(2-formyl-3-hydroxy-phenoxy)methyl]benzoic acid, and its analog are immune modulators. These compounds can be readily prepared according to methods and procedures details in U.S. Pat. No. 4,535,183, which is incorporated herein by reference in its entirety. In some embodiments, these compounds can enhance co-stimulatory signaling to CD4-positive and CD8-positive T-cells, leading to tumor-cell-killing. In some embodiments, these compounds can provide a costimulatory signal to $CD4^+$ T-cells and $CD8^+$ T-cells, activating $Na^+$ and $K^+$ transport, converging with T-cell receptor (TCR) signaling at the level of the MAP kinase ERK-2, and priming for increased intensity of calcium signaling. In some embodiments, these compounds can be biologically active as an immunopotentiator, favoring a Th1 response in patients with malignant melanoma.

Plinabulin, (3Z,6Z)-3-Benzylidene-6-{[5-(2-methyl-2-propanyl)-1H-imidazol-4-yl]methylene}-2,5-piperazinedione, is a synthetic analog of the natural compound phenylahistin. Plinabulin can be readily prepared according to methods and procedures detailed in U.S. Pat. Nos. 7,064,201 and 7,919,497, which are incorporated herein by reference in their entireties. In some embodiments, Plinabulin can efficiently promote antigen uptake and migration of dendritic cells to lymph nodes where tumor-specific antigens are presented by dendritic cells to primeimmune effector cells. Exposure of dendritic cells to Plinabulin can induce maturation of dendritic cells and significantly increase their capacity to prime T cells. In some embodiments, Plinabulin can mediate tumor size reduction through immune modulation of the tumor microenvironment to promote anti-tumor immune enhancing effects. In some embodiments, substantial therapeutic synergies can be achieved when combining Plinabulin with immune checkpoint inhibitors.

Some embodiments relate to the use of a compound of formula (I) in combination with one or more immune checkpoint inhibitors, such as inhibitors of CTLA4 (cytotoxic T lymphocyte antigen-4), PD1 (programmed cell death protein 1), PD-L1 (programmed cell death ligand 1), PD-L2 (programmed cell death ligand 2), PD-L3 (programmed cell death ligand 3), PD-L4 (programmed cell death ligand 4), LAG-3 (lymphocyte activation gene-3), and TIM-3 (T cell immunoglobulin and mucin protein-3). In some embodiments, the compound of Formula (I) is tucaresol. In some embodiments, the immune checkpoint inhibitor is a binding ligand of PD-1. In some embodiments, the immune checkpoint inhibitor is a binding ligand of CTLA-4. Some embodiments relate to the use of a compound of Formula (I) in combination with plinabulin. Some embodiments relate to the use of a compound of Formula (I) in combination with one or more immune checkpoint inhibitor and plinabulin. Some embodiments relate to the use of tucaresol in combination with plinabulin. Some embodiments relate to the use of tucaresol in combination with one or more immune checkpoint inhibitor and plinabulin. Some embodiments relate to the use of a compound of Formula (I) in combination with a PD-1 inhibitor or PD-L1 inhibitor. Some embodiments relate to the use of a compound of Formula (I) in combination with an inhibitor of PD-1 or PD-L1, and an inhibitor of CTLA-4. Some embodiments relate to the use of a compound of Formula (I) in combination with an inhibitor of PD-1, an inhibitor of PD-L1, and an inhibitor of CTLA-4.

Some embodiments relate to the use of tucaresol in combination with a PD-1 inhibitor or PD-L1 inhibitor. In some embodiments, no other additional checkpoint inhibitors are administered. Having no other additional check point inhibitors in the treatment may help to achieve an effective treatment with reduced or minimal toxicity. In some embodiments, no inhibitor of CTLA-4 is administered.

Some embodiments relate to the use of tucaresol in combination with an inhibitor of PD-1 or PD-L1, and an inhibitor of CTLA-4. In some embodiments, the inhibitor of CTLA-4 is administered at a dose of less than 3 mg/kg. When the dose of the CTLA-4 inhibitor is lower than the conventional dose used for treating cancer or tumor growth (e.g., 3 mg/kg), the treatment using a combination of tucaresol, an inhibitor of PD-1 or PD-L1, and an inhibitor of CTLA-4 can lead to an increased efficacy with reduced toxicity.

Some embodiments relate to the use of tucaresol in combination with an inhibitor of PD-1 or PD-L1 and an inhibitor of CTLA-4, wherein the inhibitor of CTLA-4 is administered at a dose of about 3 mg/kg or greater. When the dose of the CTLA-4 inhibitor is the conventional dose used for treating cancer or tumor growth (e.g., 3 mg/kg), the treatment of using this combination can lead to an increased efficacy without increasing toxicity.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. The term "PD-1" as used herein includes human PD-1 (hPD-1), variants, isoforms, and species homologs of hPD-1, and analogs having at least one common epitope with hPD-1.

Various cell surface glycoprotein ligands for PD-1 have been identified, including PD-L1, PD-L2, PD-L3, and PD-L4, that are expressed on antigen-presenting cells as well as many human cancers and have been shown to downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The term "PD-L2" as used herein includes human PD-L2 (hPD-L2), variants, isoforms, and species homologs of hPD-L2, and analogs having at least one common epitope with hPD-L2. The term "PD-L3" as used herein includes human PD-L3 (hPD-L3), variants, isoforms, and species homologs of hPD-L3, and analogs having at least one common epitope with hPD-L3. The term "PD-L4" as used herein includes human PD-L4 (hPD-L4), variants, isoforms, and species homologs of hPD-L4, and analogs having at least one common epitope with hPD-L4.

CTLA-4 (cytotoxic T-lymphocyte-associated protein 4) is a protein receptor that, functioning as an immune checkpoint, downregulates the immune system. CTLA4 is found on the surface of T cells, is also a member of the immunoglobulin (Ig) superfamily; CTLA-4 comprises a single extracellular Ig domain. CTLA-4 transcripts have been found in T cell populations having cytotoxic activity, suggesting that CTLA-4 might function in the cytolytic response.

The compound of Formula (I) described herein (e.g., tucaresol) can have a synergistic effect with immune checkpoint inhibitors such as PD-1/PD-L1 antibodies when used for activating the innate immune system such as natural killer cells, mast cells, eosinophils, basophils; and the phagocytic cells include macrophages, neutrophils, and dendritic cells. Activation of the innate immune system can be effective in treating cancer or inhibiting tumor growth.

The compound of Formula (I) described herein (e.g., tucaresol) can have a synergistic effect with immune checkpoint inhibitors such as PD-1/PD-L1 antibodies when used for inhibiting tumor growth. In addition, the compound of Formula (I) can also have a synergistic effect with both the immune checkpoint inhibitors PD-1 antibody and CTLA-4 antibody when used for inhibiting tumor growth. The compound of Formula (I) (e.g., tucaresol) generally can have superior anti-tumor properties over CTLA-4 antibody when used together with one or more other immune check point inhibitors and it has a better toxicity and safety profile than CTLA-4 antibody. Therefore, tucaresol can be used as a superior replacement or supplement of CTLA-4 antibody in the chemotherapy.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety. The pharmaceutically acceptable excipient can be a monosaccharide or monosaccharide derivative.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice, guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and can include curing a disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

As used herein, the term "chemotherapeutic agent" refers to an agent that reduces, prevents, mitigates, limits, and/or delays the growth of metastases or neoplasms, or kills neoplastic cells directly by necrosis or apoptosis of neoplasms or any other mechanism, or that can be otherwise used, in a pharmaceutically-effective amount, to reduce, prevent, mitigate, limit, and/or delay the growth of metastases or neoplasms in a subject with neoplastic disease. Chemotherapeutic agents include but are not limited to, for example, fluoropyrimidines; pyrimidine nucleosides; purine nucleosides; anti-folates, platinum-based agents; anthracyclines/anthracenediones; epipodophyllotoxins; camptothecins; hormones; hormonal complexes; antihormonals; enzymes, proteins, peptides and polyclonal and/or monoclonal antibodies; *vinca* alkaloids; taxanes; epothilones; antimicrotubule agents; alkylating agents; antimetabolites; topoisomerase inhibitors; antivirals; and various other cytotoxic and cytostatic agents.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —$NH_2$).

An "aminoalkyl" group refers to an amino group connected via an alkylene group.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substitutents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

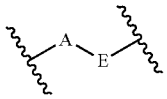

includes the substituent being oriented such that the A is attached at the leftmost attachment point of the molecule as well as the case in which A is attached at the rightmost attachment point of the molecule.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

Administration and Pharmaceutical Compositions

Some embodiments relate to a pharmaceutical composition including a compound of Formula (I) described herein and one or more immune checkpoint inhibitor. In some embodiments, the compound of Formula (I) is tucaresol. In some embodiments, the composition described herein further includes plinabulin. In some embodiments, the immune checkpoint inhibitor is an inhibitor of PD-1, PD-L1, PD-L2, PD-L3, PD-L4, CTLA-4, LAG3, B7-H3, B7-H4, KIR or TIM3. In some embodiments, the immune checkpoint inhibitor is a PD-1 inhibitor. In some embodiments, the immune checkpoint inhibitor is a binding ligand of PD-L1. In some embodiments, the immune checkpoint inhibitor is a PD-L1 inhibitor. In some embodiments, the immune checkpoint inhibitor is a PD-L2 inhibitor or a combined PD-L1/PD-L2 inhibitor. In some embodiments, the immune checkpoint inhibitor is a CTLA-4 inhibitor.

In some embodiments, the composition described herein includes a compound of Formula (I), a first immune checkpoint inhibitor and a second immune checkpoint inhibitor, wherein the first immune checkpoint inhibitor is different from the second immune checkpoint inhibitor. In some embodiments, the first and the second immune checkpoint inhibitor is independently selected from an inhibitor of PD-1, PD-L1, PD-L2, PD-L3, PD-L4, CTLA-4, LAG3, B7-H3, B7-H4, KIR or TIM3. In some embodiments, the first immune checkpoint inhibitor is a PD-1 inhibitor, and the second immune checkpoint inhibitor is a CTLA-4 inhibitor. In some embodiments, the first immune checkpoint inhibitor is a PD-L1 inhibitor, and the second immune checkpoint inhibitor is a CTLA-4 inhibitor. In some embodiments, the first immune checkpoint inhibitor is a PD-L2 inhibitor, and the second immune checkpoint inhibitor is a CTLA-4 inhibitor.

In some embodiments, the composition described herein can include the compound of formula (I) and an inhibitor of PD1. In some embodiments, the composition described herein can include the compound of formula (I) and an inhibitor of PD-L1. In some embodiments, the composition described herein can include the compound of formula (I), an inhibitor of PD-1 or PD-L1, and an inhibitor of CTLA-4. In some embodiments, the PD-1 inhibitor is pembrolizumab. In some embodiments, the PD-1 inhibitor is nivolumab. In some embodiments, the PD-L1 inhibitor is atezolizumab. In some embodiments, the CTLA-4 inhibitor is ipilimumab.

In some embodiments, the immune checkpoint inhibitor can be a small peptide agent that can inhibit T cell regulation function. In some embodiments, the immune checkpoint inhibitor can be a small molecule (e.g. less than 500 Daltons) that can inhibit T cell regulation function. In some embodiments, the immune checkpoint inhibitor can be a molecule providing co-stimulation of T-cell activation. In some embodiments, the immune checkpoint inhibitor can be a molecule providing co-stimulation of natural killer cell activation. In some embodiments, the immune checkpoint inhibitor can be an antibody. In some embodiments, the immune checkpoint inhibitor is a PD-1 antibody. In some embodiments, the immune checkpoint inhibitor is a PD-L1 antibody. In some embodiments, the immune checkpoint inhibitor is a PD-L2 antibody. In some embodiments, the immune checkpoint inhibitor is a PD-L3 antibody. In some embodiments, the immune checkpoint inhibitor is a PD-L4 antibody. In some embodiments, the immune checkpoint inhibitor is a CTLA-4 antibody. In some embodiments, the immune checkpoint inhibitor is an antibody of CTLA-4, LAG3, B7-H3, B7-H4, KIR, or TIM3.

The antibody can be selected from α-CD3-APC, α-CD3-APC-H7, α-CD4-ECD, α-CD4-PB, α-CD8-PE-Cy7, α-CD-8-PerCP-Cy5.5, α-CD11c-APC, α-CD11b-PE-Cy7, α-CD11b-AF700, α-CD14-FITC, α-CD16-PB, α-CD19-AF780, α-CD19-AF700, α-CD20-PO, α-CD25-PE-Cy7, α-CD40-APC, α-CD45-Biotin, Streptavidin-BV605, α-CD62L-ECD, α-CD69-APC-Cy7, α-CD80-FITC, α-CD83-Biotin, Streptavidin-PE-Cy7, α-CD86-PE-Cy7, α-CD86-PE, α-CD123-PE, α-CD154-PE, α-CD161-PE, α-CTLA4-PE-Cy7, α-FoxP3-AF488 (clone 259D), IgG-isotype-AF488, α-ICOS (CD278)-PE, α-HLA-A2-PE, α-HLA-DR-PB, α-HLA-DR-PerCPCy5.5, α-PD1-APC, VISTA, co-stimulatory molecule OX40, and CD137.

A variety of antibodies (Abs) can be used in the composition described herein, including antibodies having high-affinity binding to PD-1, PD-L1, PD-L2, PD-L3, or PD-L4. Human mAbs (HuMAbs) that bind specifically to PD-1 (e.g., bind to human PD-1 and may cross-react with PD-1 from other species, such as cynomolgus monkey) with high affinity have been disclosed in U.S. Pat. No. 8,008,449, which is incorporated herein by reference in its entirety. HuMAbs that bind specifically to PD-L1 with high affinity have been disclosed in U.S. Pat. No. 7,943,743, which is incorporated herein by reference in its entirety. Other anti-PD-1 mAbs have been described in, for example, U.S. Pat. Nos. 6,808,710, 7,488,802 and 8,168,757, and PCT Publication No. WO 2012/145493, all of which are incorporated herein by reference in their entireties. Anti-PD-L1 mAbs have been described in, for example, U.S. Pat. Nos. 7,635, 757 and 8,217,149, U.S. Publication No. 2009/0317368, and PCT Publication Nos. WO 2011/066389 and WO 2012/14549, all of which are incorporated herein by reference in their entireties.

In some embodiments, the anti-PD-1 HuMAbs can be selected from 17D8, 2D3, 4H1, 5C$_4$ (also referred to herein as nivolumab), 4A1 1, 7D3 and 5F4, all of which are described in U.S. Pat. No. 8,008,449. In some embodiments, the anti-PD-1 HuMAbs can be selected from 3G10, 12A4 (also referred to herein as BMS-936559), 10A5, 5F8, 10H10, 1B12, 7H1, 1 1E6, 12B7, and 13G4, all of which are described in U.S. Pat. No. 7,943,743.

Some embodiments relate to a pharmaceutical composition comprising a compound of Formula (I) and plinabulin. In some embodiments, the compound of Formula (I) is tucaresol.

In some embodiments, the composition can further include one or more pharmaceutically acceptable diluents. In some embodiments, the pharmaceutically acceptable diluent can include Kolliphor HS15® (Polyoxyl (15)-hydroxystearate). In some embodiments, the pharmaceutically acceptable diluent can include propylene glycol. In some embodiments, the pharmaceutically acceptable diluents can include kolliphor and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of Plinabulin or pharmaceutically acceptable salts thereof; (b) an immune checkpoint inhibitor and (c) a pharmaceutically acceptable carrier, diluent, excipient or combination thereof.

Other embodiments include co-administering a compound of Formula (I) and one or more immune checkpoint inhibitor in separate compositions. In some embodiments, the compound of Formula (I) is tucaresol. Thus, some embodiments include a first pharmaceutical compositions comprising: (a) a safe and therapeutically effective amount of the compound of Formula (I) or pharmaceutically acceptable salts thereof and (b) a pharmaceutically acceptable carrier, diluent, excipient or combination thereof; and a second pharmaceutical composition comprising: (a) one or more immune checkpoint inhibitor and (b) a pharmaceutically acceptable carrier, diluent, excipient or combination thereof.

Other embodiments include co-administering a compound of Formula (I) and plinabulin in separate compositions. In some embodiments, the compound of Formula (I) is tucaresol. Thus, some embodiments include a first pharmaceutical compositions comprising: (a) a safe and therapeutically effective amount of the compound of Formula (I) or pharmaceutically acceptable salts thereof and (b) a pharmaceutically acceptable carrier, diluent, excipient or combination thereof; and a second pharmaceutical composition comprising: (a) plinabulin and (b) a pharmaceutically acceptable carrier, diluent, excipient or combination thereof.

Other embodiments include co-administering a compound of Formula (I), one or more immune checkpoint inhibitor, and plinabulin in separate compositions. In some embodiments, the compound of Formula (I) is tucaresol. Thus, some embodiments include a first pharmaceutical compositions comprising: (a) a safe and therapeutically effective amount of the compound of Formula (I) or pharmaceutically acceptable salts thereof and (b) a pharmaceutically acceptable carrier, diluent, excipient or combination thereof; and a second pharmaceutical composition comprising: (a) one or more immune checkpoint inhibitor and (b) a pharmaceutically acceptable carrier, diluent, excipient or combination thereof; and a third pharmaceutical composition comprising: (a) plinabulin and (b) a pharmaceutically acceptable carrier, diluent, excipient or combination thereof.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, or intraocularly. Oral and parenteral administrations are customary in treating the indications that are the subject of the preferred embodiments.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, sublingual, buccal, nasal, rectal, topical (including transdermal and intradermal), ocular, intracerebral, intracranial, intrathecal, intraarterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g. solid gel capsules and liquid gel capsules), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

In some embodiments, the compositions described herein can be used in combination with other therapeutic agents. In some embodiments, the compositions described herein can be administered or used in combination with treatments such as chemotherapy, radiation, and biologic therapies.

Method of Treatment

Some embodiments relate to a method for treating cancer using the pharmaceutical composition described herein to a subject in need thereof. Some embodiments relate to a method for treating cancer, comprising co-administering a compound of Formula (I) described herein and one or more immune checkpoint inhibitor to a subject in need thereof. Some embodiments relate to a method for treating cancer, comprising co-administering a compound of Formula (I), one or more immune checkpoint inhibitor, and plinabulin to a subject in need thereof. Some embodiments relate to a method for treating cancer, comprising co-administering a compound of Formula (I) and plinabulin to a subject in need thereof. In some embodiments, the compound of Formula (I) is tucaresol. In some embodiments, the subject can be an animal, e.g., a mammal, a human. In some embodiments, the subject is a human.

Some embodiments relate to methods of providing co-stimulation of T-cell activation against cancer by co-administering a compound of formula (I), one or more immune checkpoint inhibitor. Some embodiments relate to methods of providing co-stimulation of natural killer cells against cancer by co-administering a compound of formula (I), one or more immune checkpoint inhibitor. In some embodiments, the compound of Formula (I) is tucaresol.

In some embodiments, the cancer comprises cancer cells expressing a binding ligand of PD-1. In some embodiments, the binding ligand of PD-1 is PD-L1. In some embodiments, the binding ligand of PD-1 is PD-L2.

In some embodiments, the method of treating cancer described herein further includes identifying cancer cells expressing a binding ligand of PD-1. In some embodiments, the method of treating cancer described herein further includes identifying cancer cells expressing PD-L1. In some embodiments, the method of treating cancer described herein further includes identifying cancer cells expressing PD-L2. In some embodiments, the method of treating cancer described herein further includes identifying cancer cells expressing PD-L3 or PD-L4.

In some embodiments, identifying cancer cells expressing a binding ligand of PD-1 includes using an assay to detect the presence of the binding ligand. Examples of applicable assay include but are not limited to PD-L1 IHC 22C₃ pharmDx kit and PD-L1 IHC 28-8 pharmDx available from Dako.

In some embodiments, the cancer comprises cancer calls expressing a binding ligand of CTLA-4. In some embodiments, the binding ligand of CTLA-4 is B7.1 or B7.2.

In some embodiments, the method of treating cancer described herein further includes identifying cancer cells expressing a binding ligand of CTLA-4. In some embodiments, the method of treating cancer described herein further includes identifying cancer cells expressing B7.1 or B7.2.

In some embodiments, the immune checkpoint inhibitor is nivolumab, pembrolizumab, pidilizumab, ipilimumab, dacarbazine, BMS 936559, atezolizumab, durvalimumab, or any combinations thereof.

In some embodiments, cancer is head and neck cancer, lung cancer, stomach cancer, colon cancer, pancreatic cancer, prostate cancer, breast cancer, kidney cancer, bladder cancer, ovary cancer, cervical cancer, melanoma, glioblastoma, myeloma, lymphoma, or leukemia. In some embodiments, the cancer is renal cell carcinoma, malignant melanoma, non-small cell lung cancer (NSCLC), ovarian cancer, Hodgkin's lymphoma or squamous cell carcinoma. In some embodiments, the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma. In some embodiments, the cancer is a solid tumor or hematological cancer.

In some embodiments, the cancer does not have any cells expressing PD-1, PD-L1, or PD-L2 at detectable levels.

In some embodiments, the combination of a compound of Formula (I) and PD-1 inhibitor (or PD-L1 inhibitor/PD-L2 inhibitor) exhibits better safety profile and lower toxicity than the combination of CTLA-4 and PD-1 inhibitor (or PD-L1 inhibitor/PD-L2 inhibitor). In some embodiments, the therapeutic index for the combination of a compound of Formula (I) and PD-1 inhibitor (or PD-L1 inhibitor/PD-L2 inhibitor) is greater than the therapeutic index of the combination of CTLA-4 and PD-1 inhibitor (or PD-L1 inhibitor/PD-L2 inhibitor). In some embodiments, the compound of Formula (I) is tucaresol.

Some embodiments relate to a method of disrupting cancer associated tumor vasculature in a subject comprising co-administering to the subject a compound of Formula (I) described herein and plinabulin. In some embodiments, the method of disrupting cancer associated tumor vasculature further includes administering one or more immune checkpoint inhibitor. In some embodiments, the compound of Formula (I) is tucaresol.

Various cancers are associated the formation of tumor vasculature. In some embodiments, the cancer is the cancer is selected from the group consisting of a melanoma, a pancreatic cancer, a colorectal adenocarcinoma, a brain tumor, acute lymphoblastic leukemia, chronic lymphocytic leukemia, hormone refractory metastatic prostate cancer, metastatic breast cancer, non-small cell lung cancer, renal cell carcinoma, head and neck cancer, prostate cancer, colon cancer, anaplastic thyroid cancer.

Some embodiments include co-administering a composition, and/or pharmaceutical composition described herein, with an additional medicament. For example, as described above, some embodiments include co-administering a compound of Formula (I) described herein with one or more immune checkpoint inhibitor, some embodiments include co-administering a compound of Formula (I) described herein with one or more immune checkpoint inhibitor and plinabulin, and some embodiments include co-administering a compound of Formula (I) described herein with plinabulin. In some embodiments, the compound of Formula (I) is tucaresol. By "co-administration," it is meant that the two or more agents are administered in such a manner that administration of one or more agent has an effect on the efficacy and/or safety of the one or more other agent, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally or intravenously. In another embodiment, the agents are administered through different routes, such as one being administered orally and another being administered i.v. In some embodiments, the time period between administration of one or more agent and administration of the co-administered one or more agent can be about 5 min, 10 min, 20 min, 30 min, 40 min, 50 min, 1 hour, 2 hours, 3 hours, 5 hours, 8 hours, 10 hours, 12 hours, 15 hours, 18 hours, 20 hours, 24 hours, 36 hours, 48 hours, 3 days, 4 days, 5 days, 6 days, 7 days, 10 days, 14 days, 21 days, 28 days, or 30 days. In some embodiments, the time period between administration of one or more agent and administration of the co-administered one or more agent can be in the range of about 1 min-5 min, 1 min-10 min, 1 min-20 min, 1 min-30 min, 1 min-40 min, 1 min-50 min, 1 min-1 h, 1 min-2 h, 1 min-4 h, 1 min-6 h, 1 min-8 h, 1 min-10 h, 1 min-12 h, 1 min-24 h, 1 min-36 h, 1 min-48 h, 1 min-60 h, 1 min-72 h, 5 min-10 min, 5 min-20 min, 5 min-30 min, 5 min-40 min, 5 min-50 min, 5 min-1 h, 5 min-2 h, 5 min-4 h, 5 min-6 h, 5 min-8 h, 5 min-10 h, 5 min-12 h, 5 min-24 h, 5 min-36 h, 5 min-48 h, 5 min-60 h, 5 min-72 h, 10 min-20 min, 10 min-30 min, 10 min-40 min, 10 min-50 min, 10 min-1 h, 10 min-2 h, 10 min-4 h, 10 min-6 h, 10 min-8 h, 10 min-10 h, 10 min-12 h, 10 min-24 h, 10 min-36 h, 10 min-48 h, 10 min-60 h, 10 min-72 h, 30 min-40 min, 30 min-50 min, 30 min-1 h, 30 min-2 h, 30 min-4 h, 30 min-6 h, 30 min-8 h, 30 min-10 h, 30 min-12 h, 30 min-24 h, 30 min-36 h, 30 min-48 h, 30 min-60 h, 30 min-72 h, 1 h-2 h, 1 h-4 h, 1 h-6 h, 1 h-8 h, 1 h-10 h, 1 h-12 h, 1 h-24 h, 1 h-36 h, 1 h-48 h, 1 h-60 h, 1 h-72 h, 6 h-8 h, 6 h-10 h, 6 h-12 h, 6 h-24 h, 6 h-36 h, 6 h-48 h, 6 h-60 h, 6 h-72 h, 12 h-24 h, 12 h-36 h, 12 h-48 h, 12 h-60 h, or 12 h-72 h.

The actual dose of the active compounds described herein depends on the specific compound, and on the condition to be treated; the selection of the appropriate dose is well within the knowledge of the skilled artisan. In some embodiments, the method described herein comprises administering the compound of Formula (I) at a dose in the range of from about 0.01 mg/kg to about 250 mg/kg of body weight, from about 0.1 mg/kg to about 200 mg/kg of body weight, from about 0.25 mg/kg to about 120 mg/kg of body weight, from about 0.5 mg/kg to about 70 mg/kg of body weight, from about 1.0 mg/kg to about 50 mg/kg of body weight, from about 1.0 mg/kg to about 15 mg/kg of body weight, from about 2.0 mg/kg to about 15 mg/kg of body weight, from about 3.0 mg/kg to about 12 mg/kg of body weight, or from about 5.0 mg/kg to about 10 mg/kg of body weight. In some embodiments, the method described herein comprises administering the compound of Formula (I) at a dose in the range of 0.5-1, 0.5-2, 0.5-3, 0.5-4, 0.5-5, 0.5-6, 0.5-7, 0.5-8, 0.5-9, 0.5-10, 1-2, 1-3, 1-4, 1-5, 1-6, 1-7, 1-8, 1-9, 1-10, 1-20, 1-30, 1-40, 1-50, 1-60, 1-70, 1-80, 1-90, 1-100, 2.5-5, 2.5-10, 2.5-20, 2.5-30, 2.5-40, 2.5-50, 2.5-60, 2.5-70, 2.5-

80, 2.5-90, 2.5-100, 3-5, 3-10, 3-20, 3-30, 3-40, 3-50, 3-60, 3-70, 3-80, 3-90, 3-100, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 80-100, 80-150, 80-200, 80-250, 80-300, 90-100, 90-150, 90-200, 90-250, 90-300, 90-350, 90-400, 100-150, 100-200, 100-250, 100-300, 100-350, or 100-400 mg/kg of body weight. In some embodiments, the compound of Formula (I) described herein may be administered at a dose of about 0.1, 0.25, 0.5, 1, 2, 3, 4, 5, 6, 7, 8, 9, 10, 11, 12, 13, 14, 15, 16, 17, 18, 19, 20, 22.5, 25, 27.5, 30, 35, 40, 45, 50, 55, 60, 65, 70, 75, 80, 85, 90, 95, or 100 mg/kg of body weight. In some embodiments, the method described herein comprises administering the compound of formula (I) at a dose of about 3 mg/kg. In some embodiments, the method described herein comprises administering the compound of formula (I) at a dose of about 3 mg/kg every three weeks for a total of four doses. In some embodiments, the compound of Formula (I) is tucaresol.

In some embodiments, the compound of Formula (I) (e.g., tucaresol) is administered at an amount of about 0.5-1, 0.5-2, 0.5-3, 0.5-4, 0.5-5, 0.5-6, 0.5-7, 0.5-8, 0.5-9, 0.5-10, 0.2.5-3, 2.5-4, 2.5-5, 2.5-6, 2.5-7, 2.5-8, 2.5-9, 2.5-10, 3-10, 5-10, 1-10, 1-20, 1-30, 1-40, 1-50, 1-60, 1-70, 1-80, 1-90, 1-100, 2.5-10, 2.5-20, 2.5-30, 2.5-40, 2.5-50, 2.5-60, 2.5-70, 2.5-80, 2.5-90, 2.5-100, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 70-500, 70-750, 70-1000, 70-1500, 70-2000, 70-3000, 80-100, 80-150, 80-200, 80-250, 80-300, 80-500, 80-750, 80-1000, 80-1500, 80-2000, 80-3000, 90-100, 90-150, 90-200, 90-250, 90-300, 90-350, 90-400, 90-500, 90-750, 90-1000, 90-1500, 90-2000, 90-3000, 100-150, 100-200, 100-250, 100-300, 100-350, 100-400, 100-500, 100-600, 100-700, 100-800, 100-900, 100-1000, 100-1500, 100-2000, 100-2500, 100-3000, 100-3500, 100-4000, 200-500, 200-700, 200-1000, 200-1500, 200-2000, 200-2500, 200-3000, 200-3500, 200-4000, 500-1000, 500-1500, 500-2000, 500-2500, 500-3000, 500-3500, or 500-4000 mg per dose. In some embodiments, the compound of Formula (I) is administered at an amount of about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 12.5, 15, 17.5, 20, 22.5, 25, 27.5, 30, 40, 50, 60, 70, 80, 90, 100, 150, 200, 250, 300, 350, 400, 450, 500, 550, 600, 650, 700, 750, 800, 850, 900, 1000, 1100, 1200, 1250, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 mg per dose. In some embodiments, the compound of formula (I) is administered at an amount of about 25 mg, 50 mg, or 100 mg per dose.

In some embodiments, the method described herein comprises administering one or more check point inhibitors at a doze in the range of about 0.5-1, 0.5-2, 0.5-3, 0.5-4, 0.5-5, 0.5-6, 0.5-7, 0.5-8, 0.5-9, 0.5-10, 1-2, 1-3, 1-4, 1-5, 1-6, 1-7, 1-8, 1-9, 1-10, 1-20, 1-30, 1-40, 1-50, 1-60, 1-70, 1-80, 1-90, 1-100, 2-3, 2-4, 2-5, 2-6, 2-7, 2-8, 2-9, 2-10, 2-20, 2-30, 2-40, 2-50, 2-60, 2-70, 2-80, 2-90, 2-100, 2.5-3, 2.5-3.5, 2.5-4, 2.5-5, 2.5-6, 2.5-7, 2.5-9, 2.5-10, 3-4, 3-5, 3-6, 3-7, 3-8, 3-9, 3-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 80-100, 80-150, 80-200, 80-250, 80-300, 90-100, 90-150, 90-200, 90-250, 90-300, 90-350, 90-400, 100-150, 100-200, 100-250, 100-300, 100-350, or 100-400 mg/kg of the body weight. In some embodiments, the method described herein comprised administering one or more checkpoint inhibitors at a dose of about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 12.5, 15, 17.5, 20, 22.5, 25, 27.5, 30, 40, 50, 60, 70, 80, 90 or 100 mg/kg of the body weight.

In some embodiments, the one or more check point inhibitor are administered at an amount of about 0.5-1, 0.5-2, 0.5-3, 0.5-4, 0.5-5, 0.5-6, 0.5-7, 0.5-8, 0.5-9, 0.5-10, 1-10, 1-20, 1-30, 1-40, 1-50, 1-60, 1-70, 1-80, 1-90, 1-100, 1-150, 1-200, 1-250, 1-300, 1-500, 2.5-3, 2.5-4, 2.5-5, 2.5-6, 2.5-7, 2.5-8, 2.5-9, 2.5-10, 2.5-20, 2.5-30, 2.5-40, 2.5-50, 2.5-60, 2.5-70, 2.5-80, 2.5-90, 2.5-100, 2.5-200, 2.5-250, 2.5-300, 2.5-500, 3-10, 3-20, 3-30, 3-40, 3-50, 3-60, 3-70, 3-80, 3-90, 3-100, 3-200, 3-250, 3-300, 3-500, 5-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 70-500, 70-750, 70-1000, 70-1500, 70-2000, 70-3000, 80-100, 80-150, 80-200, 80-250, 80-300, 80-500, 80-750, 80-1000, 80-1500, 80-2000, 80-3000, 90-100, 90-150, 90-200, 90-250, 90-300, 90-350, 90-400, 90-500, 90-750, 90-1000, 90-1500, 90-2000, 90-3000, 100-150, 100-200, 100-250, 100-300, 100-350, 100-400, 100-500, 100-600, 100-700, 100-800, 100-900, 100-1000, 100-1500, 100-2000, 100-2500, 100-3000, 100-3500, 100-4000, 200-500, 200-700, 200-1000, 200-1500, 200-2000, 200-2500, 200-3000, 200-3500, 200-4000, 500-1000, 500-1500, 500-2000, 500-2500, 500-3000, 500-3500, or 500-4000 mg per dose. In some embodiments, the one or more check point inhibitors are administered at an amount of about 1, 2, 3, 4, 5, 6, 7, 8, 9, 10, 12, 14, 16, 18, 20, 22, 25, 27, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 1100, 1200, 1300, 1400, 1500, 1600, 1700, 1800, 1900, or 2000 mg per dose.

In some embodiments, the method described herein comprises administering an inhibitor of PD-1 at a dose in the range of about 0.5-1, 0.5-2, 0.5-3, 0.5-4, 0.5-5, 0.5-6, 0.5-7, 0.5-8, 0.5-9, 0.5-10, 1-2, 1-3, 1-4, 1-5, 1-6, 1-7, 1-8, 1-9, 1-10, 1-20, 1-30, 1-40, 1-50, 1-60, 1-70, 1-80, 1-90, 1-100, 2-3, 2-4, 2-5, 2-6, 2-7, 2-8, 2-9, 2-10, 2-20, 2-30, 2-40, 2-50, 2-60, 2-70, 2-80, 2-90, 2-100, 2.5-3, 2.5-3.5, 2.5-4, 2.5-5, 2.5-6, 2.5-7, 2.5-9, 2.5-10, 3-4, 3-5, 3-6, 3-7, 3-8, 3-9, 3-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 80-100, 80-150, 80-200, 80-250, 80-300, 90-100, 90-150, 90-200, 90-250, 90-300, 90-350, 90-400, 100-150, 100-200, 100-250, 100-300, 100-350, or 100-400 mg/kg of the body weight. In some embodiments, the method described herein comprises administering the inhibitor of PD-1 at a dose of about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 12.5, 15, 17.5, 20, 22.5, 25, 27.5, 30, 40, 50, 60, 70, 80, 90 or 100 mg/kg of the body weight. In some embodiments, the inhibitor of PD-1 is administered at a dose of about 3 mg/kg. In some embodiments, the inhibitor of PD-1 is administered at a dose of about 2 mg/kg.

In some embodiments, the PD-1 inhibitor is administered at an amount of about 1-10, 1-20, 1-30, 1-40, 1-50, 1-60, 1-70, 1-80, 1-90, 1-100, 1-150, 1-200, 1-250, 1-300, 1-500, 2.5-3, 2.5-4, 2.5-5, 2.5-6, 2.5-7, 2.5-8, 2.5-9, 2.5-10, 2.5-20, 2.5-30, 2.5-40, 2.5-50, 2.5-60, 2.5-70, 2.5-80, 2.5-90, 2.5-100, 2.5-200, 2.5-250, 2.5-300, 2.5-500, 3-10, 3-20, 3-30, 3-40, 3-50, 3-60, 3-70, 3-80, 3-90, 3-100, 3-200, 3-250, 3-300, 3-500, 5-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 70-500, 70-750, 70-1000, 70-1500, 70-2000, 70-3000, 80-100, 80-150, 80-200, 80-250, 80-300, 80-500, 80-750, 80-1000, 80-1500, 80-2000, 80-3000, 90-100, 90-150, 90-200, 90-250, 90-300, 90-350, 90-400, 90-500, 90-750, 90-1000, 90-1500, 90-2000, 90-3000, 100-150, 100-200, 100-250, 100-300, 100-350, 100-400, 100-500, 100-600, 100-700, 100-800, 100-900, 100-1000, 100-1500, 100-2000, 100-2500, 100-3000, 100-3500, 100-4000, 200-500, 200-700, 200-1000, 200-1500, 200-2000, 200-2500, 200-3000, 200-3500, 200-4000, 500-1000, 500-1500, 500-2000, 500-2500, 500-3000, 500-3500, or 500-4000 mg per dose. In some embodiments, the PD-1 inhibitor is administered at an amount of about 10-30, 10-50, 10-80, 10-100, 10-125, 10-150, 10-175, 10-200, 10-250, 10-300, 10-400, 20-50, 20-100, 20-125, 20-150, 20-175, 20-200, 20-250, 20-300, 20-400, 30-50, 30-80, 30-100, 30-125, 30-150, 30-175, 30-200, 30-250, 30-300, 30-400, 40-50, 40-80, 40-100, 40-125, 40-150, 40-175, 40-200, 40-250, 40-300, 40-400, 50-80, 50-100, 50-125, 50-150, 50-175, 50-200, 50-250, 50-300, or 50-400 mg per dose.

In some embodiments, the method described herein comprises administering an inhibitor of PD-L1 at a dose in the range of about 0.5-1, 0.5-2, 0.5-3, 0.5-4, 0.5-5, 0.5-6, 0.5-7, 0.5-8, 0.5-9, 0.5-10, 1-2, 1-3, 1-4, 1-5, 1-6, 1-7, 1-8, 1-9, 1-10, 1-20, 1-30, 1-40, 1-50, 1-60, 1-70, 1-80, 1-90, 1-100, 2-3, 2-4, 2-5, 2-6, 2-7, 2-8, 2-9, 2-10, 2-20, 2-30, 2-40, 2-50, 2-60, 2-70, 2-80, 2-90, 2-100, 2.5-3, 2.5-3.5, 2.5-4, 2.5-5, 2.5-6, 2.5-7, 2.5-9, 2.5-10, 3-4, 3-5, 3-6, 3-7, 3-8, 3-9, 3-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 80-100, 80-150, 80-200, 80-250, 80-300, 90-100, 90-150, 90-200, 90-250, 90-300, 90-350, 90-400, 100-150, 100-200, 100-250, 100-300, 100-350, or 100-400 mg/kg of the body weight. In some embodiments, the method described herein comprises administering the inhibitor of PD-L1 at a dose of about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 12.5, 15, 17.5, 20, 22.5, 25, 27.5, 30, 40, 50, 60, 70, 80, 90 or 100 mg/kg of the body weight.

In some embodiments, the PD-L1 inhibitor (e.g., atezolizumab) is administered at an amount of about 1-10, 1-20, 1-30, 1-40, 1-50, 1-60, 1-70, 1-80, 1-90, 1-100, 1-150, 1-200, 1-250, 1-300, 1-500, 2.5-3, 2.5-4, 2.5-5, 2.5-6, 2.5-7, 2.5-8, 2.5-9, 2.5-10, 2.5-20, 2.5-30, 2.5-40, 2.5-50, 2.5-60, 2.5-70, 2.5-80, 2.5-90, 2.5-100, 2.5-200, 2.5-250, 2.5-300, 2.5-500, 3-10, 3-20, 3-30, 3-40, 3-50, 3-60, 3-70, 3-80, 3-90, 3-100, 3-200, 3-250, 3-300, 3-500, 5-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 70-500, 70-750, 70-1000, 70-1500, 70-2000, 70-3000, 80-100, 80-150, 80-200, 80-250, 80-300, 80-500, 80-750, 80-1000, 80-1500, 80-2000, 80-3000, 90-100, 90-150, 90-200, 90-250, 90-300, 90-350, 90-400, 90-500, 90-750, 90-1000, 90-1500, 90-2000, 90-3000, 100-150, 100-200, 100-250, 100-300, 100-350, 100-400, 100-500, 100-600, 100-700, 100-800, 100-900, 100-1000, 100-1500, 100-2000, 100-2500, 100-3000, 100-3500, 100-4000, 200-500, 200-700, 200-1000, 200-1500, 200-2000, 200-2500, 200-3000, 200-3500, 200-4000, 500-1000, 500-1500, 500-2000, 500-2500, 500-3000, 500-3500, or 500-4000 mg per dose. In some embodiments, the PD-L1 inhibitor is administered at an amount of about 500-1500, 600-1500, 700-1500, 800-1500, 900-1500, 1000-1500, or 1100-1300 mg per dose. In some embodiments, the PD-L1 inhibitor is administered at an amount of about 1200 mg per dose.

In some embodiments, the method described herein comprises administering the inhibitor of CTLA-4 (e.g., ipilimumab) at a dose in the range of about 0.5-1, 0.5-2, 0.5-3, 0.5-4, 0.5-5, 0.5-6, 0.5-7, 0.5-8, 0.5-9, 0.5-10, 1-2, 1-3, 1-4, 1-5, 1-6, 1-7, 1-8, 1-9, 1-10, 1-20, 1-30, 1-40, 1-50, 1-60, 1-70, 1-80, 1-90, 1-100, 2-3, 2-4, 2-5, 2-6, 2-7, 2-8, 2-9, 2-10, 2-20, 2-30, 2-40, 2-50, 2-60, 2-70, 2-80, 2-90, 2-100, 2.5-3, 2.5-3.5, 2.5-4, 2.5-5, 2.5-6, 2.5-7, 2.5-9, 2.5-10, 3-4, 3-5, 3-6, 3-7, 3-8, 3-9, 3-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300 mg/kg of the body weight. In some embodiments, the method described herein comprises administering the inhibitor of CTLA-4 at a dose of about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 12.5, 15, 17.5, 20, 22.5, 25, 27.5, 30, 40, 50, 60, 70, 80, 90 or 100 mg/kg of the body weight. In some embodiments, the inhibitor of CTLA-4 is administered at a dose of about 3 mg/kg. In some embodiments, the inhibitor of CTLA-4 is administered at a dose of lower than 3 mg/kg. In some embodiments, the inhibitor of CTLA-4 is administered at a dose of about 0.5, 1, 1.5, 2, or 2.5 mg/kg.

In some embodiments, the CTLA-4 inhibitor is administered at an amount of about 1-10, 1-20, 1-30, 1-40, 1-50, 1-60, 1-70, 1-80, 1-90, 1-100, 1-150, 1-200, 1-250, 1-300, 1-500, 2.5-3, 2.5-4, 2.5-5, 2.5-6, 2.5-7, 2.5-8, 2.5-9, 2.5-10, 2.5-20, 2.5-30, 2.5-40, 2.5-50, 2.5-60, 2.5-70, 2.5-80, 2.5-90, 2.5-100, 2.5-200, 2.5-250, 2.5-300, 2.5-500, 3-10, 3-20, 3-30, 3-40, 3-50, 3-60, 3-70, 3-80, 3-90, 3-100, 3-200, 3-250, 3-300, 3-500, 5-10, 5-10, 5-20, 5-30, 5-40, 5-50, 5-60, 5-70, 5-80, 5-90, 5-100, 7.5-10, 7.5-20, 7.5-30, 7.5-40, 7.5-50, 7.5-60, 7.5-70, 7.5-80, 7.5-90, 7.5-100, 10-10, 10-20, 10-30, 10-40, 10-50, 10-60, 10-70, 10-80, 10-90, 10-100, 10-150, 10-200, 20-30, 20-40, 20-50, 20-60, 20-70, 20-80, 20-90, 20-100, 20-150, 20-200, 30-40, 30-50, 30-60, 30-70, 30-80, 30-90, 30-100, 30-150, 30-200, 40-50, 40-60, 40-70, 40-80, 40-90, 40-100, 40-150, 40-200, 40-300, 50-60, 50-70, 50-80, 50-90, 50-100, 50-150, 50-200, 50-250, 50-300, 60-80, 60-100, 60-150, 60-200, 70-100, 70-150, 70-200, 70-250, 70-300, 70-500, 70-750, 70-1000, 70-1500, 70-2000, 70-3000, 80-100, 80-150, 80-200, 80-250, 80-300, 80-500, 80-750, 80-1000, 80-1500, 80-2000, 80-3000, 90-100, 90-150, 90-200, 90-250, 90-300, 90-350, 90-400, 90-500, 90-750, 90-1000, 90-1500, 90-2000, 90-3000, 100-150, 100-200, 100-250, 100-300, 100-350, 100-400, 100-500, 100-600, 100-700, 100-800, 100-900, 100-1000, 100-1500, 100-2000, 100-2500, 100-3000, 100-3500, 100-4000, 200-500, 200-700, 200-1000, 200-1500, 200-2000, 200-2500, 200-3000, 200-3500, 200-4000, 500-1000, 500-1500, 500-2000, 500-2500, 500-3000, 500-3500, or 500-4000 mg per dose. In some embodiments, the CTLA-4 inhibitor is administered at an amount of about 10-30, 10-50, 10-80, 10-100, 10-125, 10-150, 10-175, 10-200, 10-250, 10-300, 10-400, 20-50, 20-100, 20-125, 20-150, 20-175, 20-200, 20-250, 20-300, 20-400, 30-50, 30-80, 30-100, 30-125, 30-150, 30-175, 30-200, 30-250, 30-300, 30-400, 40-50, 40-80, 40-100, 40-125, 40-150, 40-175, 40-200, 40-250, 40-300, 40-400, 50-80, 50-100, 50-125, 50-150, 50-175, 50-200, 50-250, 50-300, or 50-400 mg per dose.

In some embodiments, the treatment schedule includes co-administration of the compound of formula (I) (e.g., tucaresol) and one or more checkpoint inhibitors (e.g., PD-1/PD-L1 inhibitor and CTLA-4 inhibitor) once every 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors once every 2 weeks or 3 weeks. In some embodiments, the treatment schedule includes co-administration of the compound of formula (I) and one or more checkpoint inhibitors two times every 1 week, 2 weeks, 3 weeks, 4 weeks, 5 weeks, 6 weeks, 7 weeks, or 8 weeks. In some embodiments, the treatment schedule includes co-administration of a chemotherapeutic agent and plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors twice every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors three times every 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors four times every 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors five times every 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors six times every 1 week, 2 weeks, 3 weeks, 4 weeks, 5 weeks, 6 weeks, 7 weeks, or 8 weeks. In some embodiments, the treatment schedule includes co-administration of the compound of formula (I) and one or more checkpoint inhibitors daily every 1 week, 2 weeks, 3 weeks, or 4 weeks. In some embodiments, co-administration of the compound of formula (I) and one or more checkpoint inhibitors includes administering the compound of formula (I) prior to administering the one or more checkpoint inhibitors. In some embodiments, the treatment schedule includes co-administration of the compound of formula (I) and one or more checkpoint inhibitors 1, 2, 3, 4, 5, 6, or 7 times per day. In some embodiments, the treatment schedule includes co-administration of the compound of formula (I) and one or more checkpoint inhibitors once every 2, 3, 4, 5, or 6 days.

In some embodiments, co-administration of the compound of formula (I) and one or more checkpoint inhibitors includes administering the compound of formula (I) after administering the one or more checkpoint inhibitors. In some embodiments, co-administration of the compound of formula (I) and one or more checkpoint inhibitors includes administering the compound of formula (I) concurrently with the one or more checkpoint inhibitors. When more than one checkpoint inhibitors are administered, the two check point inhibitors can be administered separately or concurrently.

In some embodiments, when the compound of formula (I) is administered prior to the one or more checkpoint inhibitors are administered, the one or more checkpoint inhibitors can be administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h after the administration of the compound of formula (I). In some embodiments, the one or more checkpoint inhibitors are administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11h, 12 h, 13 h, 14 h, 15 h, 16 h, 17 h, 18 h, 19 h, 20 h, 21 h, 22 h, 23 h, or 24 h after the administration of the compound of formula (I). In some embodiments, the one or more checkpoint inhibitors are administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, or 24 h after the administration of the compound of formula (I). In some embodiments, the one or more checkpoint inhibitors are administered in about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h after the administration of the compound of formula (I). In some embodiments, the one or more checkpoint inhibitors are administered in about 1 min-5 min, 1 min-10 min, 1 min-20 min, 1 min-30 min, 1 min-40 min, 1 min-50 min, 1 min-1 h, 1 min-2 h, 1 min-4 h, 1 min-6 h, 1 min-8 h, 1 min-10 h, 1 min-12 h, 1 min-24 h, 1 min-36 h, 1 min-48 h, 1 min-60 h, 1 min-72 h, 5 min-10 min, 5 min-20 min, 5 min-30 min, 5 min-40 min, 5 min-50 min, 5 min-1 h, 5 min-2 h, 5 min-4 h, 5 min-6 h, 5 min-8 h, 5 min-10 h, 5 min-12 h, 5 min-24 h, 5 min-36 h, 5 min-48 h, 5 min-60 h, 5 min-72 h, 10 min-20 min, 10 min-30 min, 10 min-40 min, 10 min-50 min, 10 min-1 h, 10 min-2 h, 10 min-4 h, 10 min-6 h, 10 min-8 h, 10 min-10 h, 10 min-12 h, 10 min-24 h, 10 min-36 h, 10 min-48 h, 10 min-60 h, 10 min-72 h, 30 min-40 min, 30 min-50 min, 30 min-1 h, 30 min-2 h, 30 min-4 h, 30 min-6 h, 30 min-8 h, 30 min-10 h, 30 min-12 h, 30 min-24 h, 30 min-36 h, 30 min-48 h, 30 min-60 h, 30 min-72 h, 1 h-2 h, 1 h-4 h, 1 h-6 h, 1 h-8 h, 1 h-10 h, 1 h-12 h, 1 h-24 h, 1 h-36 h, 1 h-48 h, 1 h-60 h, 1 h-72 h, 6 h-8 h, 6 h-10 h, 6 h-12 h, 6 h-24 h, 6 h-36 h, 6 h-48 h, 6 h-60 h, 6 h- 72 h, 12 h-24 h, 12 h-36 h, 12 h-48 h, 12 h-60 h, or 12 h-72 h after the administration of the compound of formula (I).

In some embodiments, when the one or more checkpoint inhibitors are administered prior to the compound of formula (I) is administered, the one or more checkpoint inhibitors are administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, or 1 h-5 h before the administration of the compound of formula (I). In some embodiments, the one or more checkpoint inhibitors are administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, or 12 h before the administration of the compound of formula (I). In some embodiments, the one or more checkpoint inhibitors are administered less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11h, 12 h, 13 h, 14 h, 15 h, 16 h, 17 h, 18 h, 19 h, 20 h, 21 h, 22 h, 23 h, or 24 h before the administration of the compound of formula (I). In some embodiments, the one or more checkpoint inhibitors are administered more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11h, 12 h, 13 h, 14 h, 15 h, 16 h, 17 h, 18 h, 19 h, 20 h, 21 h, 22 h, 23 h, or 24 h before the administration of the compound of formula (I). In some embodiments, the one or more checkpoint inhibitors are administered in about 1 min-5 min, 1 min-10 min, 1 min-20 min, 1 min-30 min, 1 min-40 min, 1 min-50 min, 1 min-1 h, 1 min-2 h, 1 min-4 h, 1 min-6 h, 1 min-8 h, 1 min-10 h, 1 min-12 h, 1 min-24 h, 1 min-36 h, 1 min-48 h, 1 min-60 h, 1 min-72 h, 5 min-10 min, 5 min-20 min, 5 min-30 min, 5 min-40 min, 5 min-50 min, 5 min-1 h, 5 min-2 h, 5 min-4 h, 5 min-6 h, 5 min-8 h, 5 min-10 h, 5 min-12 h, 5 min-24 h, 5 min-36 h, 5 min-48 h, 5 min-60 h, 5 min-72 h, 10 min-20 min, 10 min-30 min, 10 min-40 min, 10 min-50 min, 10 min-1 h, 10 min-2 h, 10 min-4 h, 10 min-6 h, 10 min-8 h, 10 min-10 h, 10 min-12 h, 10 min-24 h, 10 min-36 h, 10 min-48 h, 10 min-60 h, 10 min-72 h, 30 min-40 min, 30 min-50 min, 30 min-1 h, 30 min-2 h, 30 min-4 h, 30 min-6 h, 30 min-8 h, 30 min-10 h, 30 min-12 h, 30 min-24 h, 30 min-36 h, 30 min-48 h, 30 min-60 h, 30 min-72 h, 1 h-2 h, 1 h-4 h, 1 h-6 h, 1 h-8 h, 1 h-10 h, 1 h-12 h, 1 h-24 h, 1 h-36 h, 1 h-48 h, 1 h-60 h, 1 h-72 h, 6 h-8 h, 6 h-10 h, 6 h-12 h, 6 h-24 h, 6 h-36 h, 6 h-48 h, 6 h-60 h, 6 h-72 h, 12 h-24 h, 12 h-36 h, 12 h-48 h, 12 h-60 h, or 12 h-72 h before the administration of the compound of formula (I).

The treatment cycle can be repeated as long as the regimen is clinically tolerated. In some embodiments, the treatment cycle for the compound of formula (I) and the one or more checkpoint inhibitors is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a washout period can occur before starting a new treatment cycle. In some embodiments, the washout period can be 1 week, 2 weeks, 3 weeks, or 4 weeks. In some embodiments, the dose of the compound of formula (I) can be the same for each treatment cycle. In some embodiments, the dose of the compound of formula (I) can be different in each treatment cycle (e.g., the dose can be 20 mg for the first treatment cycle, 50 mg for the second treatment cycle, 100 mg for the third treatment cycle).

In some embodiments, after the compound of formula (I) and the one or more checkpoint inhibitors are administered in one cycle of treatment, the next treatment cycle may include administering only the compound of formula (I). In some embodiments, after the compound of formula (I) and the one or more checkpoint inhibitors are administered in one cycle of treatment, the next treatment cycle may include administering both the compound of formula (I) and the one or more checkpoint inhibitors.

In some embodiments, the compound of formula (I) (e.g., tucaresol) is administered at a dose of about 3 mg/kg every three weeks as a treatment cycle and the treatment cycle is repeated four times. In some embodiments, the one or more checkpoint inhibitors (e.g., any one of PD-1 inhibitor, PD-L1 inhibitor, CTLA-4 inhibitor, and any combinations thereof) can be co-administered with the compound of formula (I) in each treatment cycle, In some embodiments, the one or more checkpoint inhibitors can be co-administered with the compound of formula (I) in half of the treatment cycles (e.g. the first and the third treatment cycles).

In some embodiments, the method described herein can include one or more additional medicaments. Examples of additional medicaments include other chemotherapeutic agents.

In some embodiments, the chemotherapeutic agent can be selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Cabazitaxel, Cabozantinib-S-Malate, CAF, Campath (Alemtuzumab), Camptosar (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cobimetinib, Cometriq (Cabozantinib-S-Malate), COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Decitabine, Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idelalisib, Ifex (Ifosfamide), Ifosfamide, IL-2 (Aldesleukin), Imatinib Mesylate, Imbruvica (Ibrutinib), Imiquimod, Imlygic (Talimogene Laherparepvec), Inlyta (Axitinib), Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Netupitant and Palonosetron Hydrochloride, Neupogen (Filgrastim), Nexavar (Sorafenib Tosylate), Nilotinib, Ninlaro (Ixazomib Citrate), Nivolumab, Nolvadex (Tamoxifen Citrate), Nplate (Romiplostim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, Pegaspargase, Peginterferon Alfa-2b, PEG-Intron (Peginterferon Alfa-2b), Pembrolizumab, Pemetrexed Disodium Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituximab, Rolapitant Hydrochloride, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thioguanine, Thiotepa, Tolak (Fluorouracil—Topical), Toposar (Etoposide), Topotecan Hydrochloride, Toremifene, Torisel (Temsirolimus), Tositumomab and Iodine I 131, Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1. Effects on Tumor and Non-Tumor Cell Viability

1) Tucaresol

Tucaresol (0-1200 µM) is exposed for 72 hours to a panel of human liquid, hematological, and solid tumors such as multiple myeloma, leukemia, colorectal, non-small cell lung cancer (squamous and adenocarcinoma), hepatocellular, renal, pancreatic and breast cancer cell lines, and human non-tumor such as HUVEC, PBMC, skin fibroblast cells lines. Tucaresol is studied either alone or in combination with standard-of-care agents (1-100 µM). All cell lines are grown in standard serum-containing media with an exposure time of 24-144 hours. Cell viability is measured using, for example, the Cell TiterGlo® Viability Assay. The potency ($IC_{50}$) and efficacy (% cell kill) are determined from the percent cell growth of the vehicle control.

2) Tucaresol Plus PD-1 Antibody

Tucaresol (0-1200 µM) in the presence of a PD-1 antibody is exposed for 72 hours to a panel of human liquid, hematological, and solid tumor such as multiple myeloma, leukemia, colorectal, non-small cell lung cancer (squamous and adenocarcinoma), hepatocellular, renal, pancreatic and breast cancer cell lines, and human non-tumor such as HUVEC, PBMC, skin fibroblast cells lines, and the viability of the cell lines are measured as described above. The viability of the cell lines in the presence of tucaresol plus PD-1 antibody is compared to the viability of the cell lines in the presence of a CTLA-4 antibody plus the PD-1 antibody or PD-1 antibody alone.

3) CTLA-4 Antibody Plus PD-1 Antibody

CTLA-4 antibody in the presence of a PD-1 antibody is exposed for 72 hours to a panel of human liquid, hematological, and solid tumor such as multiple myeloma, leukemia, colorectal, non-small cell lung cancer (squamous and adenocarcinoma), hepatocellular, renal, pancreatic and breast cancer cell lines, and human non-tumor such as HUVEC, PBMC, skin fibroblast cells lines, and the viability of the cell lines are measured as described above.

4) Tucaresol Plus Plinabulin

Tucaresol (0-1200 µM) in the presence of Plinabulin is exposed for 72 hours to a panel of human liquid, hematological, and solid tumor such as multiple myeloma, leukemia, colorectal, non-small cell lung cancer (squamous and adenocarcinoma), hepatocellular, renal, pancreatic and breast cancer cell lines, and human non-tumor such as HUVEC, PBMC, skin fibroblast cells lines, and the viability of the cell lines are measured as described above.

The viability of the cell lines in the presence of tucaresol, tucaresol plus PD-1 antibody, CTLA-4 antibody plus the PD-1 antibody, and tucaresol plus plinabulin are compared.

Example 2. Potentiation of T Cell Proliferative Responses

Five groups including tucaresol, tucaresol plus PD-1 or PD-L1 antibody, tucaresol plus CTLA-4 antibody, CTLA-4 antibody plus PD-1 or PD-L1 antibody, and tucaresol plus plinabulin are tested to determine the potentiation of T cell proliferative response.

Markers for cell maturation (CD40, CD80, CD86, MHC II) are measured by FACS analysis in the SP37A3 immature mouse dendritic cell (DC) cell line after 20 hours of incubation with the test compounds. The assays are performed as described by Martin et al., *Cancer Immuno Immunothe* (2014) 63(9):925-38. (2014) and Müller et al, *Cancer Immunol Res* (2014) 2(8), 741-55. Compounds are prepared as a 10 mM stock solution in DMSO and subsequently diluted to the final concentration in cell culture medium for use in the cell line studies and were examined using serial dilution over a concentration range of 1 nM to 10 µM.

Example 3. Induction of In Vitro Cytokine Production by CD4 and CD8 T Cells

Five groups including tucaresol, tucaresol plus PD-1 or PD-L1 antibody, tucaresol plus CTLA-4 antibody, CTLA-4 antibody plus PD-1 or PD-L1 antibody, and tucaresol plus plinabulin are tested to determine the effects on in vitro cytokine production by CD4 and CD8 T cells (e.g, IFN-gamma and IL-2 cells).

The release of pro-inflammatory cytokines (IL-1β, IL-6, IL 12p40) is quantified by ELISA. The assays are performed as described by Martin et al., *Cancer Immuno Immunothe* (2014) 63(9):925-38. (2014) and Müller et al, *Cancer Immunol Res* (2014) 2(8), 741-55. Compounds are prepared as a 10 mM stock solution in DMSO and subsequently diluted to the final concentration in cell culture medium for use in the cell line studies and are examined using serial dilution over a concentration range of 1 nM to 10 μM.

Example 4. Synergy of Tucaresol and Immune Checkpoint Inhibitors (PD-1 Antibody/PD-L1 Antibody)

The combined treatment with tucaresol and a PD-1 or PD-L1 checkpoint inhibitor is tested in comparison with the treatment with tucaresol alone and the treatment with PD-1 antibody or PD-L1 antibody alone. The tests are performed using seven to ten-week old immune competent mice that are injected subcutaneously with MC-38 tumor cells. Seven testing groups are prepared, and each group includes 10 mice.

Group 1 is administered with saline; Group 2 is administered with the tucaresol diluent (in the absence of tucaresol); Group 3 is administered with tucaresol dissolved in diluent at a concentration of 5 mg/kg; Group 4 is administered with tucaresol dissolved in diluent at a concentration of 10 mg/kg; Group 5 is administered with PD-1 antibody (or PD-L1 antibody); Group 6 is administered with a tucaresol 5 mg/kg/PD-1 antibody (or PD-L1 antibody) combined treatment; and Group 7 is administered with a tucaresol 10 mg/kg/PD-1 antibody (or PD-L1 antibody) combined treatment. For the tucaresol/PD-1 antibody (or PD-L1 antibody) combined treatments (Groups 6 and 7), the mice are administered every other day for 9 treatments with tucaresol (5 or 10 mg/kg) that is dissolved in diluent, followed by administering PD-1 antibody (or PD-L1 antibody) one hour after each tucaresol administration on Days 1 and 3 of each week. For the tucaresol only treatment (Groups 3 and 4) or the antibody only treatment (Group 5), mice are administered tucaresol (5 or 10 mg/kg dissolved in diluent) every other day for 9 treatments or antibody alone twice per week (Day 1 and Day 3 of each week). For Groups 1 and 2, the mice are administered with saline or the tucaresol diluent alone twice per week.

Each treatment starts at tumor size between 10-500 mm$^3$ and continues until Day 24-56. To determine the efficacy of each treatment, the following data are collected: mortality rate; the body weight of the mice assessed twice weekly both prior to treatments; the rate of tumor growth as determined by the tumor size measurement (twice every week); the tumor growth index; overall survival rate; the time required to double tumor size and the tumor weight at necropsy.

Example 5. Synergy of Tucaresol and Immune Checkpoint Inhibitors (PD-1 Antibody/PD-L1 Antibody and CTLA-4 Antibody)

The combined treatment with tucaresol, a PD-1 checkpoint inhibitor (or PD-L1 antibody), and a CTLA-4 checkpoint inhibitor is tested in comparison with the treatment with tucaresol alone, the treatment with PD-1 antibody (or PD-L1 antibody) alone, or the treatment with PD-1 antibody (or PD-L1 antibody) in combination with CTLA-4 antibody. The tests are performed using seven to ten-week old immune competent mice that were injected subcutaneously with MC-38 tumor cells. Six testing groups are prepared, and each group includes 10 mice.

Group 1 is administered with IgG2a and tucaresol vehicle; Group 2 is administered with tucaresol dissolved in diluent at a concentration of 5 mg/kg; Group 3 is administered with tucaresol dissolved in diluent at a concentration of 10 mg/kg; Group 4 is administered with PD-1 antibody (or PD-L1 antibody); Group 5 is administered with a tucaresol (5 mg/kg)/PD-1 antibody (or PD-L1 antibody) combined treatment; group 6 is administered with a tucaresol (10 mg/kg)/PD-1 antibody (or PD-L1 antibody) combined treatment; Group 7 is administered combined PD-1 (or PD-L1)/CTLA-4 antibodies; and Group 8 is administered with a tucaresol (5 mg/kg)/PD-1 antibody (or PD-L1 antibody)/CTLA-4 antibody combined treatment; and Group 9 is administered with tucaresol (10 mg/kg)/PD-1 antibody (or PD-L1 antibody)/CTLA-4 antibody combined treatment. For the tucaresol/PD-1 antibody (or PD-L1 antibody) combined treatment (Groups 5 and 6) and the tucaresol/PD-1 antibody (or PD-L1 antibody)/CTLA-4 antibody treatment (Groups 8 and 9), the mice are administered every other day with tucaresol (5 or 10 mg/kg) that is dissolved in diluent, for 9 treatments, followed by administering antibody (ies) one hour after each tucaresol administration on Days 1 and 3 of each week. For the tucaresol only treatment (Groups 2 and 3) or the antibody (ies) only treatment (Groups 4 and 7), mice are administered with tucaresol (5 or 10 mg/kg dissolved in diluent) every other day for 9 treatments or antibody (ies) alone on Day 1 and Day 3 of each week.

Each treatment starts at tumor size between 40-150 mm$^3$ and continues until Day 24-56, when the animals are necropsied. To determine the efficacy of each treatment, the following data are collected: mortality; the body weight of the mice assessed twice weekly both prior to treatments; the rate of tumor growth as determined by the tumor size measurement (twice every week); the tumor growth index; overall survival rate; the tumor weight at necropsy; and the time required to increase tumor size 10 fold. At necropsy the tissues are weighed and subjected to FACS analysis.

Example 6. Synergy of Tucaresol and Plinabulin

The combined treatment with tucaresol and Plinabulin is tested in comparison with the treatment with tucaresol alone and Plinabulin alone. The tests are performed using seven to ten-week old immune competent mice that are injected subcutaneously with MC-38 tumor cells. Seven testing groups are prepared, and each group includes 10 mice.

Group 1 is administered with saline; Group 2 is administered with the tucaresol diluent (in the absence of tucaresol); Group 3 is administered with tucaresol dissolved in diluent at a concentration of 5 mg/kg; Group 4 is administered with tucaresol dissolved in diluent at a concentration of 10 mg/kg; Group 5 is administered with Plinabulin; Group 6 is administered with a tucaresol 5 mg/kg, and Plinabulin; and Group 7 is administered with a tucaresol 10 mg/kg and Plinabulin.

Each treatment starts at tumor size between 40-150 mm$^3$ and continues until Day 24-56. To determine the efficacy of each treatment, the following data are collected: mortality rate; the body weight of the mice assessed twice weekly both prior to treatments; the rate of tumor growth as determined by the tumor size measurement (twice every week); the tumor growth index; overall survival rate; the time required to double tumor size and the tumor weight at necropsy.

Example 7. Effects in Animal Xenograft Models

Five groups including tucaresol, tucaresol plus PD-1 or PD-L1 antibody, tucaresol plus CTLA-4 antibody, CTLA-4 antibody plus PD-1 or PD-L1 antibody, and tucaresol plus plinabulin are tested to determine their effect in an animal xenograft model.

The combined treatment with tucaresol and the checkpoint inhibitor(s) is tested in comparison with the treatment with tucaresol alone, the treatment with checkpoint inhibitor alone, or combination of checkpoint inhibitors. The tests are performed using seven to ten-week old athymic (nu/nu) mice that were injected subcutaneously with human tumor cell lines (of either solid or liquid tumor origin, for example of breast, lung, colon, brain, liver, leukemia, myeloma, lymphoma, sarcoma, pancreatic or renal origin). Six to ten testing groups are prepared, and each group includes 10 mice.

Each treatment starts at tumor size between 40-150 mm$^3$ and continues until Day 24-56, when the animals are necropsied. To determine the efficacy of each treatment, the following data are collected: mortality; the body weight of the mice assessed twice weekly both prior to treatments; the rate of tumor growth as determined by the tumor size measurement (twice every week); the tumor growth index; overall survival rate; the tumor weight at necropsy; and the time required to increase tumor size 10 fold.

Example 8. Synergy of Tucaresol and Immune Checkpoint Inhibitors

The treatment with the combination of tucaresol and a PD-1 checkpoint inhibitor and the combination of tucaresol, a PD-1 antibody, and CTLA-4 antibody were tested in comparison with treatment using PD-1 antibody alone. The tests were performed using seven to ten-week old immune competent mice that were injected subcutaneously with MC-38 tumor cells.

Four testing groups were prepared. Group 1 was administered with PD-1 antibody (3 mg/kg) alone; Group 2 was administered with a tucaresol (10 mg/kg)/PD-1 antibody (3 mg/kg) combined treatment; Group 3 was administered with a PD-1 antibody (3 mg/kg)/CTLA-4 antibody (3 mg/kg) combined treatment; Group 4 was administered with a tucaresol (10 mg/kg)/PD-1 antibody (3 mg/kg)/CTLA-4 antibody (3 mg/kg) combined treatment. For the tucaresol/PD-1 antibody and the tucaresol (10 mg/kg)/PD-1 antibody (3 mg/kg)/CTLA-4 antibody (3 mg/kg) combined treatments (Groups 2 and 4), the mice were administered tucaresol dissolved in diluent every other day for 9 treatments (10 mg/kg) followed by administering PD-1 antibody one hour after each tucaresol administration on Days 1 and 3 of each week. For the antibody only treatment (Group 1), the mice were administered PD-1 antibody (3 mg/kg dissolved in diluent) twice per week (Day 1 and Day 3 of each week).

Each treatment started at tumor size between 40-150 mm$^3$ and continued until Day 24. To determine the efficacy of each treatment, the following data were collected: mortality rate; the body weight of the mice assessed twice weekly both prior to treatments; the rate of tumor growth as determined by the tumor size measurement (twice every week); the tumor growth index; overall survival rate; the time required to double tumor size and the tumor weight at necropsy.

Figure 2:
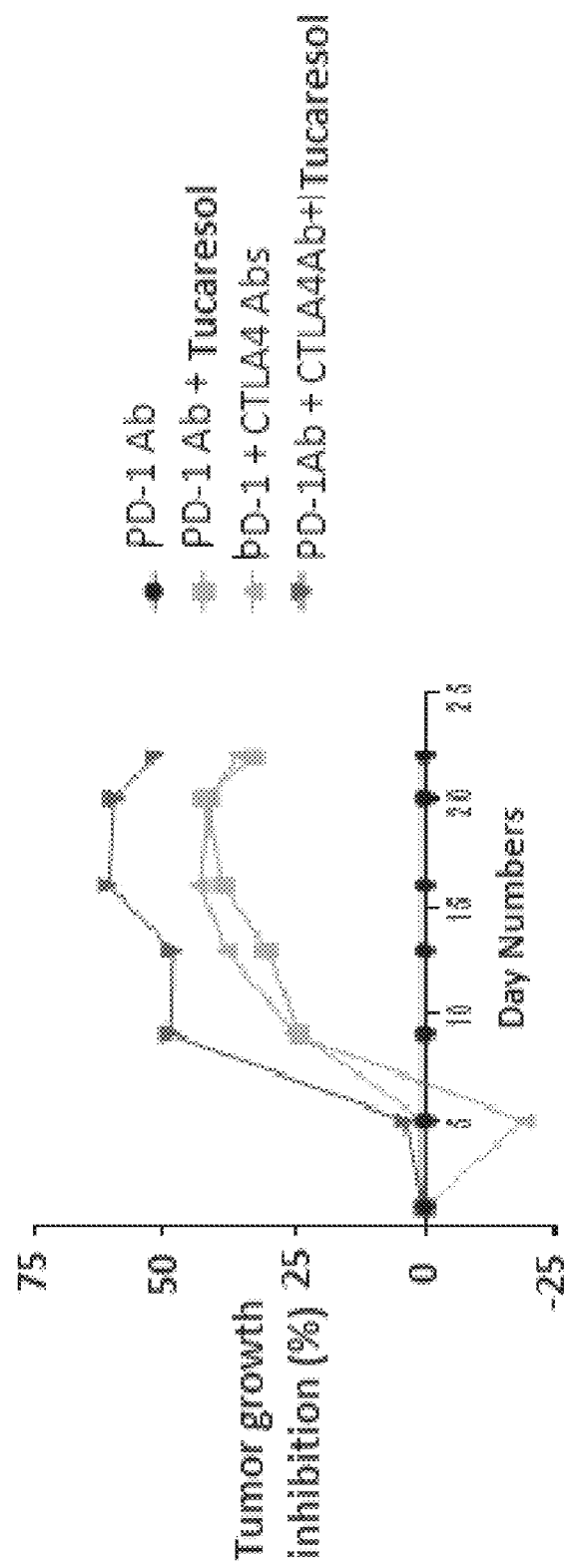
FIG. 2 shows the anti-tumor effect of each of the four treatment groups PD-1 antibody, PD-1 antibody/tucaresol, PD-1 and CTLA-4 antibodies, and PD-1 antibody/CTLA-4 antibody/tucaresol.
Figure 3:
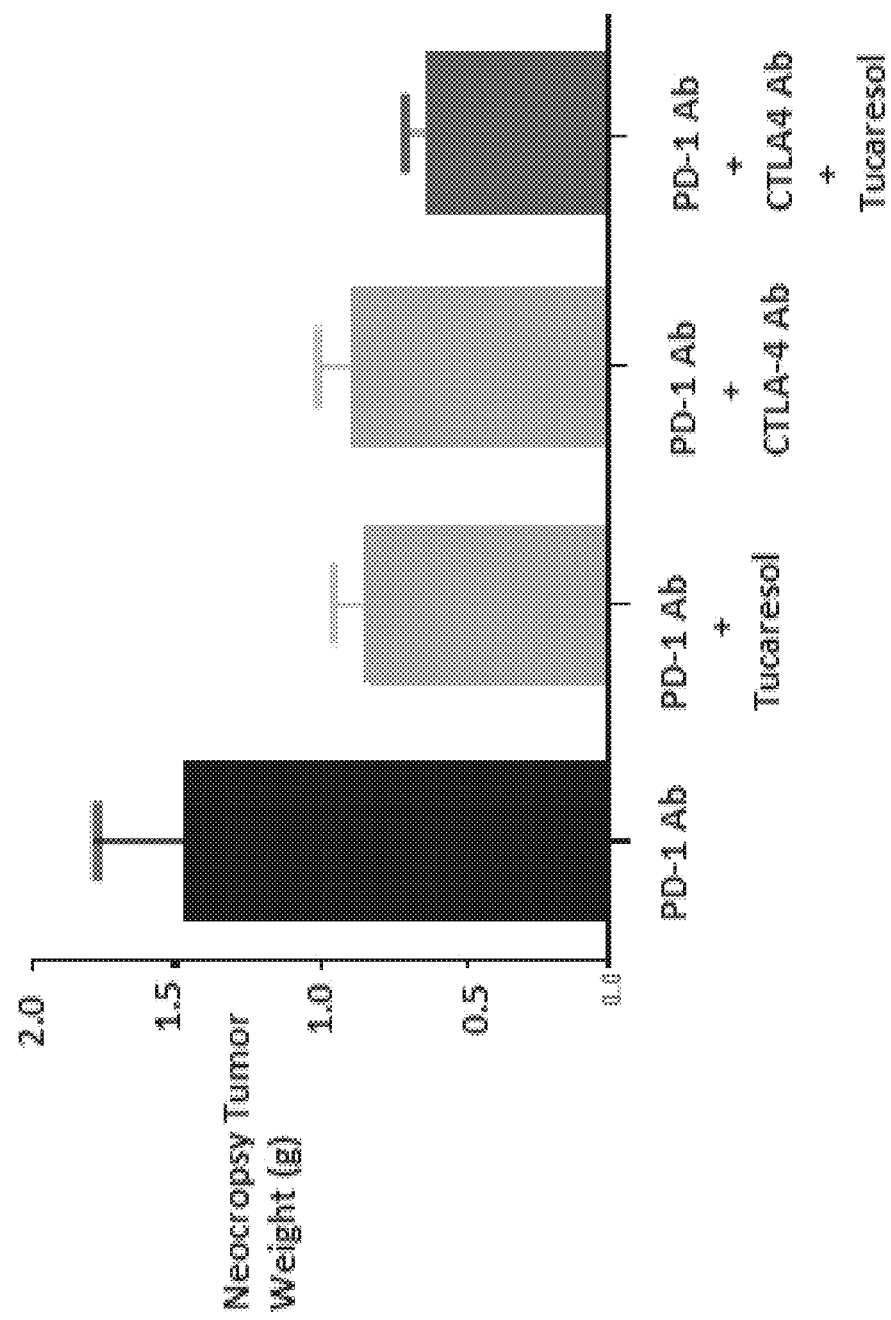
FIG. 3 shows the effect of tucaresol in combination with the PD-1 antibody on MC38 tumor weight at necropsy.

FIG. 1 shows the MC 38 tumor growth in each of the four treatment groups. FIG. 2 shows the effect of the four treatment groups on the tumor growth inhibition. FIG. 3 shows the effect of tucaresol in combination with the PD-1 antibody on MC38 tumor weight at necropsy. As illustrated in these figures, the combination of tucaresol and PD-1 antibody had an anti-tumor effect that was similar as or better than the combination of PD-1 antibody and CTLA-4 antibody, and both combinations showed better tumor growth inhibition than PD-1 antibody alone.

Example 9. Comparison of Tucaresol and CTLA-4 Antibody

The treatment with the combination of tucaresol, a PD-1 antibody, and CTLA-4 antibody was compared with the combination of PD-1 antibody and CTLA-4 antibody for their tumor inhibition effects. The tests were performed using seven to ten-week old immune competent mice that were injected subcutaneously with MC-38 tumor cells.

Three testing groups were prepared. Group A was administered with PD-1 antibody (3 mg/kg)/CTLA-4 antibody (3 mg/kg) combined treatment; Group B was administered with a tucaresol (10 mg/kg)/PD-1 antibody (3 mg/kg) CTLA-4 antibody (3 mg/kg) combined treatment; and Group C was administered with a PD-1 antibody (3 mg/kg)/CTLA-4 antibody (10 mg/kg) combined treatment. For the tucaresol (10 mg/kg)/PD-1 antibody (3 mg/kg)/CTLA-4 antibody (3 mg/kg) combined treatments, the mice were administered tucaresol dissolved in diluent (10 mg/kg) every other day for 9 treatments followed by administering PD-1 antibody one hour after each tucaresol administration on Days 1 and 3 of each week. For the PD-1 antibody and CTLA-4 antibody group, mice were administered with the antibody twice per week (Day 1 and Day 3 of each week).

Each treatment started at tumor size between 40-150 mm$^3$ and continued until Day 24. To determine the efficacy of each treatment, the following data were collected: mortality rate; the body weight of the mice assessed twice weekly both prior to treatments; the rate of tumor growth as determined by the tumor size measurement (twice every week); the tumor growth index; overall survival rate; the time required to double tumor size and the tumor weight at necropsy.

Figure 4:
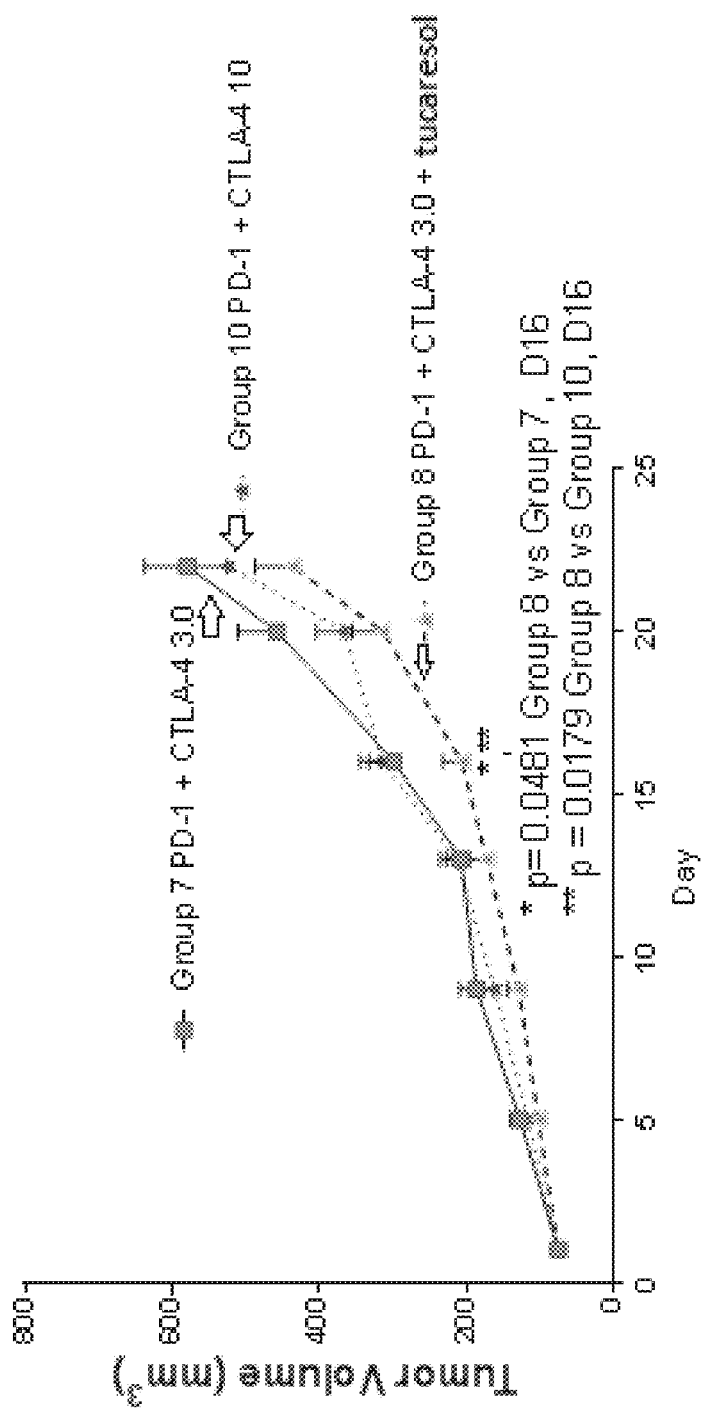
FIG. 4 shows the MC 38 tumor growth in each of three treatment groups including PD-1/CTLA-4 antibodies and PD-1 antibody/CTLA-4 antibody/tucaresol.

FIG. 4 shows the MC 38 tumor growth in each of the three treatment groups. As shown in FIG. 4, when tucaresol (10 mg/kg) was added to a combination of PD-1 (3 mg/kg) and CTLA-4 antibodies, it increased the anti-tumor effect of the combination to a greater extent than increasing the dose of the CTLA-4 antibody (from 3 mg/kg to 10 mg/kg) in the PD-1 antibody and CTLA-4 antibody combination. The results indicated that tucaresol was more effective in inhibiting tumor growth than CTLA-4 antibody when used together with the immune checkpoint inhibitors such as PD-1 antibody. Because tucaresol has better toxicity and safety profile than the CTLA-4 antibody, it can be used as a replacement or supplement of CTLA-4 antibody in the chemotherapy. The study results indicated that adding tucaresol to PD-1 antibody and CTLA-4 antibody can be more effective against the growth of MC38 tumors than increasing the dose of the CTLA-4 antibody.

What is claimed is:

1. A pharmaceutical composition, comprising a compound of Formula (I):

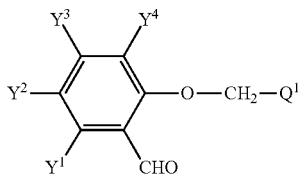

$Y^1$ is selected from hydroxyl, $C_{1-4}$ alkylamino and acylamino having a $C_{1-4}$ alkyl moiety thereof;

$Y^2$, $Y^3$ and $Y^4$ are independently selected from hydrogen, halogen, $C_{1-4}$ alkyl, $C_{1-4}$ alkoxy, trifluoromethyl, hydroxyl and benzyloxy; and $Q^1$ is either

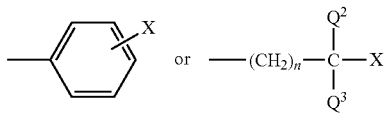

where $Q^2$ and $Q^3$ are independently selected from hydrogen and $C_{1-4}$ alkyl;

X is selected from cyano, carboxyl or a derivative thereof, 5-tetrazolyl and alkylsulfonylcarbamyl having a $C_{1-6}$ alkyl moiety thereof; and n is 0 or an integer selected from 1, 2, 3, 4, 5 and 6, and a pharmaceutically acceptable salt thereof; and one or more immune checkpoint inhibitor, wherein the one or more immune checkpoint inhibitor is an inhibitor of PD-1, PD-L1, PD-L2, or CTLA-4.

2. The composition of claim 1, comprising a first immune checkpoint inhibitor and a second immune checkpoint inhibitor, wherein the first immune checkpoint inhibitor is different from the second immune checkpoint inhibitor.

3. The composition of claim 2, wherein the first and the second immune checkpoint inhibitor is independently an inhibitor of PD-1, PD-L1, PD-L2, or CTLA-4.

4. The composition of claim 3, wherein the first immune checkpoint inhibitor is a PD-1 inhibitor, and the second immune checkpoint inhibitor is a CTLA-4 inhibitor.

5. The composition of claim 3, wherein the first immune checkpoint inhibitor is a PD-L1 inhibitor, and the second immune checkpoint inhibitor is a CTLA-4 inhibitor.

6. The composition of claim 3, wherein the first immune checkpoint inhibitor is a PD-L2 inhibitor, and the second immune checkpoint inhibitor is a CTLA-4 inhibitor.

7. The composition of claim 1, wherein the immune checkpoint inhibitor is an antibody.

8. The composition of claim 7, wherein the antibody is selected from α-CD3-APC, α-CD3-APC-H7, α-CD4-ECD, α-CD4-PB, α-CD8-PE-Cy7, α-CD-8-PerCP-Cy5.5, α-CD11c-APC, α-CD11b-PE-Cy7, α-CD11b-AF700, α-CD14-FITC, α-CD16-PB, α-CD19-AF780, α-CD19-AF700, α-CD20-PO, α-CD25-PE-Cy7, α-CD40-APC, α-CD45-Biotin, Streptavidin-BV605, α-CD62L-ECD, α-CD69-APC-Cy7, α-CD80-FITC, α-CD83-Biotin, Streptavidin-PE-Cy7, α-CD86-PE-Cy7, α-CD86-PE, α-CD123-PE, α-CD154-PE, α-CD161-PE, α-CTLA4-PE-Cy7, α-FoxP3-AF488 (clone 259D), IgG1-isotype-AF488, α-ICOS (CD278)-PE, α-HLA-A2-PE, α-HLA-DR-PB, α-HLA-DR-PerCPCy5.5, α-PD1-APC, VISTA, co-stimulatory molecule OX40, and CD137.

9. The composition of claim 1, further comprising one or more additional chemotherapeutic agent.

10. The composition of claim 1, further comprising plinabulin.

11. A method for treating cancer, comprising co-administering a compound of Formula (I):

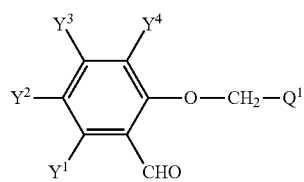

$Y^1$ is selected from hydroxyl, $C_{1-4}$ alkylamino and acylamino having a $C_{1-4}$ alkyl moiety thereof;

$Y^2$, $Y^3$ and $Y^4$ are independently selected from hydrogen, halogen, $C_{1-4}$ alkyl, $C_{1-4}$ alkoxy, trifluoromethyl, hydroxyl and benzyloxy; and $Q^1$ is either

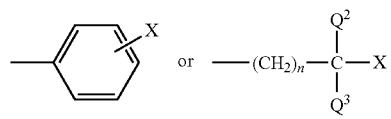

where $Q^2$ and $Q^3$ are independently selected from hydrogen and $C_{1-4}$ alkyl;

X is selected from cyano, carboxyl or a derivative thereof, 5-tetrazolyl and alkylsulfonylcarbamyl having a $C_{1-6}$ alkyl moiety thereof; and n is 0 or an integer selected from 1, 2, 3, 4, 5 and 6, and a pharmaceutically acceptable salt thereof;

one or more immune checkpoint inhibitor; and plinabulin to a subject in need thereof, wherein the one or more immune checkpoint inhibitor is an inhibitor of PD-1, PD-L1, PD-L2, PD-L3, PD-L4 or CTLA-4.

12. The method of claim 11, further comprising co-administering one or more additional chemotherapeutic agent.

13. The method of claim 11, wherein the cancer comprises cancer cells expressing a binding ligand of PD-1.

14. The method of claim 13, wherein the binding ligand of PD-1 is PD-L1 or PD-L2.

15. The method of claim 11, wherein the cancer is head and neck cancer, lung cancer, stomach cancer, colon cancer, pancreatic cancer, prostate cancer, breast cancer, kidney cancer, bladder cancer, ovary cancer, cervical cancer, melanoma, glioblastoma, myeloma, lymphoma, or leukemia.

16. The method of claim 11, wherein the cancer is renal cell carcinoma, malignant melanoma, non-small cell lung cancer (NSCLC), ovarian cancer, Hodgkin's lymphoma or squamous cell carcinoma.

17. The method of claim 11, wherein the immune checkpoint inhibitor is nivolumab, pembrolizumab, pidilizumab, ipilimumab, BMS 936559, atezolizumab, durvalumab, or any combinations thereof.

18. The method of claim 11, further comprising a second immune checkpoint inhibitor, wherein a first immune checkpoint inhibitor is different from the second immune checkpoint inhibitor.

19. The method of claim 18, wherein the first immune checkpoint inhibitor is a PD-1 inhibitor, and the second immune checkpoint inhibitor is a CTLA-4 inhibitor.

20. The method of claim 11, wherein the immune checkpoint inhibitor is an antibody.

21. The method of claim 20, wherein the immune checkpoint inhibitor is a PD-1 antibody, PD-L1 antibody, PD-L2 antibody, or CTLA-4 antibody.

22. The method of claim 20, wherein the antibody is selected from α-CD3-APC, α-CD3-APC-H7, α-CD4-ECD, α-CD4-PB, α-CD8-PE-Cy7, α-CD-8-PerCP-Cy5.5, α-CD11c-APC, α-CD11b-PE-Cy7, α-CD11b-AF700, α-CD14-FITC, α-CD16-PB, α-CD19-AF780, α-CD19-AF700, α-CD20-PO, α-CD25-PE-Cy7, α-CD40-APC, α-CD45-Biotin, Streptavidin-BV605, α-CD62L-ECD, α-CD69-APC-Cy7, α-CD80-FITC, α-CD83-Biotin, Streptavidin-PE-Cy7, α-CD86-PE-Cy7, α-CD86-PE, α-CD123-PE, α-CD154-PE, α-CD161-PE, α-CTLA4-PE-Cy7, α-FoxP3-AF488 (clone 259D), IgG1-isotype-AF488, α-ICOS (CD278)-PE, α-HLA-A2-PE, α-HLA-DR-PB, α-HLA-DR-PerCPCy5.5, α-PD1-APC, VISTA, co-stimulatory molecule OX40, and CD137.

23. The method of claim 11, wherein the compound of Formula (I) is tucaresol.

24. A method for treating cancer, comprising co-administering a compound of Formula (I):

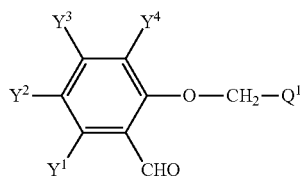

(I)

$Y^1$ is selected from hydroxyl, $C_{1-4}$ alkylamino and acylamino having a $C_{1-4}$ alkyl moiety thereof;

$Y^2$, $Y^3$ and $Y^4$ are independently selected from hydrogen, halogen, $C_{1-4}$ alkyl, $C_{1-4}$ alkoxy, trifluoromethyl, hydroxyl and benzyloxy; and $Q^1$ is either

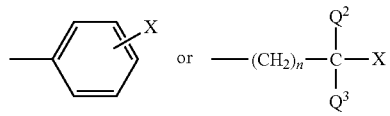

where $Q^2$ and $Q^3$ are independently selected from hydrogen and $C_{1-4}$ alkyl;

X is selected from cyano, carboxyl or a derivative thereof, 5-tetrazolyl and alkylsulfonylcarbamyl having a $C_{1-6}$ alkyl moiety thereof; and n is 0 or an integer selected from 1, 2, 3, 4, 5 and 6, and a pharmaceutically acceptable salt thereof; and plinabulin to a subject in need thereof.

25. The method of claim 24, wherein the cancer is selected from breast cancer, colon cancer, rectal cancer, lung cancer, prostate cancer, melanoma, leukemia, ovarian cancer, gastric cancer, renal cell carcinoma, liver cancer, pancreatic cancer, lymphomas and myeloma.

26. The method of claim 24, wherein the compound of Formula (I) is tucaresol.

* * * * *